(12) United States Patent
Itako et al.

(10) Patent No.: US 7,586,592 B2
(45) Date of Patent: Sep. 8, 2009

(54) SHEET RECOGNIZING DEVICE AND METHOD

(75) Inventors: Eiji Itako, Saitama (JP); Yasuyuki Kimura, Saitama (JP); Futoshi Houjo, Saitama (JP); Satoru Tsurumaki, Saitama (JP); Seiji Takamatsu, Saitama (JP)

(73) Assignee: Kabushiki Kaisha Nippon Conlux (JP)

( * ) Notice: Subject to any disclaimer, the term of this patent is extended or adjusted under 35 U.S.C. 154(b) by 351 days.

(21) Appl. No.: 11/667,845

(22) PCT Filed: Nov. 11, 2005

(86) PCT No.: PCT/JP2005/020735

§ 371 (c)(1),
(2), (4) Date: May 15, 2007

(87) PCT Pub. No.: WO2006/054495

PCT Pub. Date: May 26, 2006

(65) Prior Publication Data

US 2008/0137072 A1    Jun. 12, 2008

(30) Foreign Application Priority Data

Nov. 16, 2004   (JP)   ............................... 2004-331828

(51) Int. Cl.
*G06K 9/74*   (2006.01)
(52) U.S. Cl. ......................................... 356/71; 235/469
(58) Field of Classification Search .................. 356/71, 356/402, 403, 407; 235/435, 454, 469
See application file for complete search history.

(56) References Cited

U.S. PATENT DOCUMENTS 4,618,257 A * 10/1986 Bayne et al. .................. 356/71

(Continued)

FOREIGN PATENT DOCUMENTS

JP           54-29397          9/1979

(Continued)

*Primary Examiner*—Roy Punnoose
(74) *Attorney, Agent, or Firm*—Fish & Richardson P.C.

(57) ABSTRACT

A sheet recognizing device and method for precisely checking the authentication of a sheet by performing recognition of color and watermark of a sheet and detecting the subtle characteristic of a hue ink printed on one side of the sheet. The sheet recognizing device comprises first and third light sources for projecting light at predetermined angles to a sheet, a second light source for projecting light from a vertical direction, first and second light-receiving elements for receiving light at angles at which the hues of the hue ink printed area originated from the lights from the first and second light sources are different, a third light-receiving element opposed to the second light source with the sheet interposed therebetween, first computing means for computing a first color tone depending on the hue ink printed area on the basis of the light-reception outputs from the first light-receiving element due to the light from the first light source and from the second light-receiving element due to the light from the third light source, second computing means for computing a second color tone independent of the hue ink printed area on the basis of the light-reception outputs from the first light-receiving element due to the light from the second light source and from the third light-receiving element due to the light from the third light source, whereby the sheet is checked on the basis of the computation results by the first and second computing means.

10 Claims, 15 Drawing Sheets

U.S. PATENT DOCUMENTS

| | | | |
|---|---|---|---|
| 5,304,813 A * | 4/1994 | De Man | 250/556 |
| 5,498,879 A * | 3/1996 | De Man | 250/556 |
| 7,218,386 B2 * | 5/2007 | Alcock et al. | 356/71 |
| 2004/0051862 A1* | 3/2004 | Alcock et al. | 356/71 |
| 2006/0018508 A1* | 1/2006 | Monk et al. | 382/100 |

FOREIGN PATENT DOCUMENTS

| | | |
|---|---|---|
| JP | 59-49270 | 4/1984 |
| JP | 4-52274 | 5/1992 |
| JP | 06-060242 | 3/1994 |
| JP | 06-171071 | 6/1994 |
| JP | 06-203244 | 7/1994 |
| JP | 09-062894 | 3/1997 |

\* cited by examiner

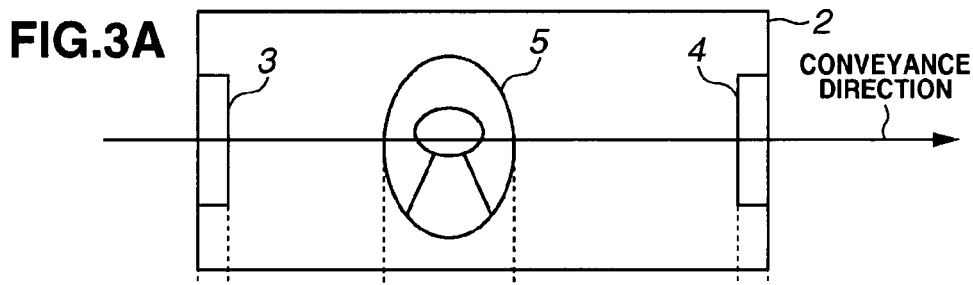

FIG. 3A

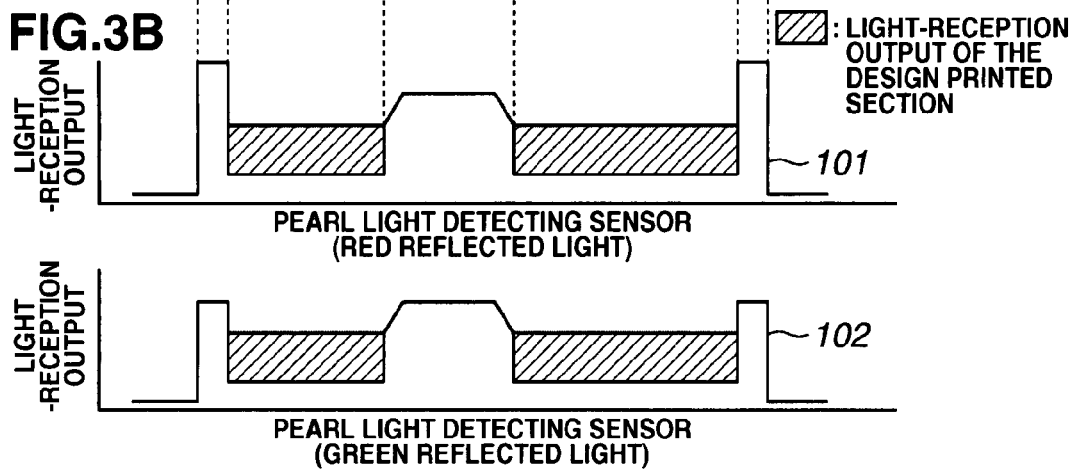

FIG. 3B

PEARL LIGHT DETECTING SENSOR
(RED REFLECTED LIGHT)

PEARL LIGHT DETECTING SENSOR
(GREEN REFLECTED LIGHT)

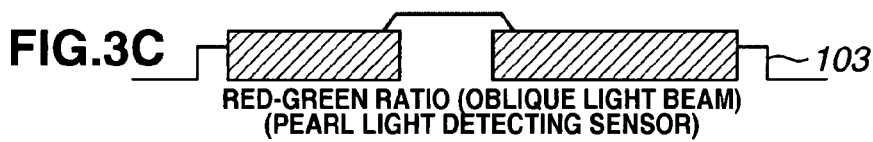

FIG. 3C

RED-GREEN RATIO (OBLIQUE LIGHT BEAM)
(PEARL LIGHT DETECTING SENSOR)

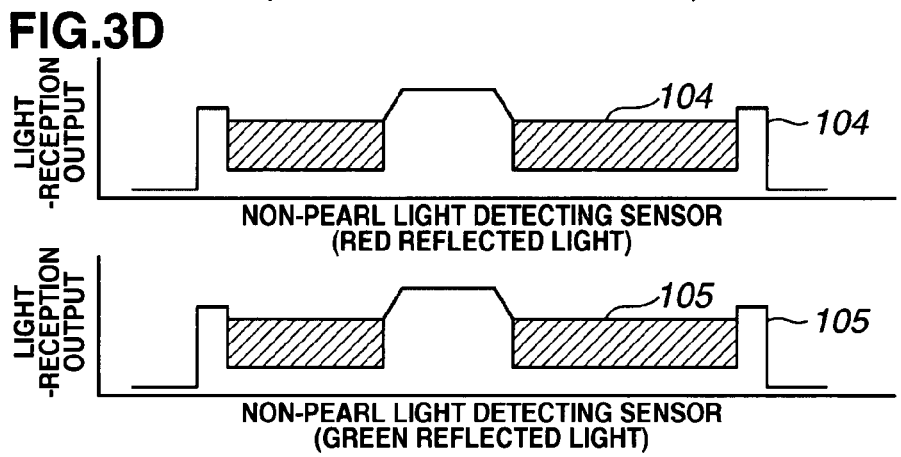

FIG. 3D

NON-PEARL LIGHT DETECTING SENSOR
(RED REFLECTED LIGHT)

NON-PEARL LIGHT DETECTING SENSOR
(GREEN REFLECTED LIGHT)

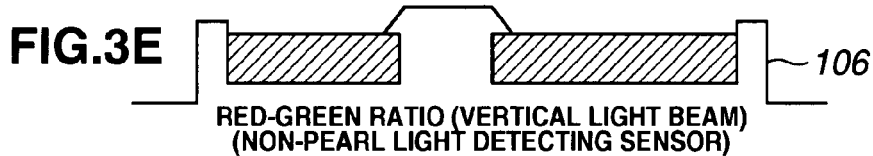

FIG. 3E

RED-GREEN RATIO (VERTICAL LIGHT BEAM)
(NON-PEARL LIGHT DETECTING SENSOR)

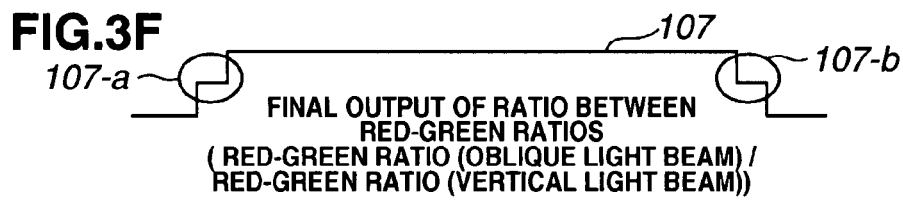

FIG. 3F

FINAL OUTPUT OF RATIO BETWEEN
RED-GREEN RATIOS
( RED-GREEN RATIO (OBLIQUE LIGHT BEAM) /
RED-GREEN RATIO (VERTICAL LIGHT BEAM))

SHEET RECOGNIZING DEVICE AND METHOD

TECHNICAL FIELD

The present invention relates to a sheet recognizing device and method, and particularly to a sheet recognizing device and method for precisely discriminating the authentication of a sheet by performing recognition of color and watermark of a sheet and detecting the subtle characteristic of a hue ink printed on one side of the sheet.

BACKGROUND ART

In recent years, due to the spread of devices such as high-accuracy scanners, printers, and computers, there are problems such as counterfeiting and misuse of securities such as bills and checks. Therefore, it is desired that a method and device for accurately recognizing these counterfeits be provided.

Recently, for the case of counterfeits made by means of copying, studies are proceeding with recognizing methods and recognizing devices capable of easily recognizing the authentication of these counterfeits. Further, there have been provided various papermaking machines and printing techniques that are designed for anticounterfeit measures, and bills and the like which are difficult to be counterfeited have been provided.

(Related Art 1)

For example, Patent Literature 1 proposes a recognizing method for recognizing an intaglio printed matter and other printed matters, in which plural light receiving elements, which receive light of the same wavelength, are disposed at different angles with respect to one another, light emitted on bills is received at the plural light receiving elements, and amounts of the received light are compared with one another, whereby the concave and convex sections on the bills are discriminated.

This proposition has a configuration such that point-like light beams are projected sequentially on a surface of the target printed matter along a certain detection line, and it is then determined whether the interrelationship among the amounts of light received at each of the plurality of positions is recognized as an interrelationship when the incident point is even, the plurality of positions being in the vicinity of an angular position, which is symmetric to the incident light, with a virtual normal line at the incident point is the center. Then, if a determination, which is that the interrelationship is not for the case where a result of completion of the detection is even, exceeds a fixed rate determined by the target printed matter, the target printed matter is determined as an intaglio printed matter.

(Related Art 2)

Patent Literature 2 proposes a printed matter reading method and apparatus in which, on a printed matter obtained by using a hue ink in which the hue changes depending on the angle of view, a pair of red and green light beams is projected onto the hue ink section, two light receiving sensors where the acceptance angles are different are used to measure the light beams to discriminate the hue ink on the basis of the difference between the colors and the reflection angle.

This proposition has a configuration such that, when a photo sensor output of the red light, for example, is larger than a photo sensor output of the green light at an observation point A, and when the magnitudes of them are reversed at an observation point B, a printed matter to be determined is determined as a regular printed matter in which specific hue inks, but when reverse of the magnitudes is not observed, the printed matter is determined as a counterfeit.

(Related Art 3)

Patent Literature 3 proposes a counterfeit recognizing device which receives both reflected light and transmitted light from a single light-emitting element and discriminates watermarks of sheets and the like.

This proposition has a configuration such that recognition of the authentication of a bill or the like is performed by reading a watermark pattern of the bill or the like by means of two optical reading means using the transmitted light and the reflected light, and comparing both data items which have been read with each other to check whether they are the same.

(Related Art 4)

Patent Literature 4 proposes a sheet recognition device which has a configuration such that discrimination of the authentication of a sheet is performed by detecting an anticounterfeit stripe provided between both sides of the sheet on the basis of the difference between pattern data, which is obtained by adding the reflection pattern data of the surface of the sheet to the reflection pattern data of the back of the sheet, and the transmission pattern data of the sheet.

Patent Literature 1: Japanese Patent Application Laid-Open No. 6-171071

Patent Literature 2: Japanese Patent Application Laid-Open No. 9-062894

Patent Literature 3: Japanese Patent Application Laid-Open No. 6-203244

Patent Literature 4: Japanese Patent Application Laid-Open No. 6-060242

DISCLOSURE OF INVENTION

Problems to be Solved by the Invention

Incidentally, the related art 1 discloses a method of receiving lights by changing the angle of the reflected light on the surfaces of the bills, the reflected light being obtained from predetermined projected light, and discriminating the concave and convex sections on the bills on the basis of whether the rate of a determination result obtained by comparing the received lights is at least a defined value. The related art 2 discloses a method of projecting a pair of red and green light beams onto the hue ink section, and discriminating the hue ink on the basis of whether the acceptance amounts of these colors, which are measured by the two light receiving sensors where the acceptance angles are different, are reversed or not.

Further, the related art 3 discloses a method of receiving both reflected light and transmitted light from a single light-emitting element, and discriminating watermarks. The related art 4 discloses a method of discriminating the authentication of a sheet by detecting an anticounterfeit stripe provided between both sides of the sheet on the basis of the difference between pattern data, which is obtained by adding the reflection pattern data of the surface of the sheet to the reflection pattern data of the back of the sheet, and the transmission pattern data of the sheet.

However, any of the propositions described in the related art 1 through the related art 4 does not describe a method of detecting the subtle characteristics of a pearl ink (ink having translucent designs on which pearl luster is observed depending on the viewing angle), which is a type of a hue ink, in which the colors that are changed are different depending on the type of the pearl ink (manufacturers and the like) and depending on the viewing angle, or in which the light-reception output of the reflected light from the light projected onto the pearl ink is different depending on the wavelength or illuminating angle of the light, to precisely recognizing a pearl ink printed on a sheet.

In order to recognize a watermark or color tone of a sheet so that a pearl ink (hue ink) printed on only one side of the sheet can be detected by using a method of disposing sensors (reflection optical sensor and transmissive optical sensor), it is required to provide two sets of the reflection optical sensor and transmissive optical sensor in which the reflection optical sensor for detecting the pearl ink printed on one side of the sheet and the transmissive optical sensor for detecting a watermark of the sheet constitute one of the sets, so that the both sides of the sheet are detected. However, this configuration complicates the control of each sensor and causes increase in power consumption, increase in the size of the device, and increase in the costs of the devices.

Moreover, if limiting the positions for disposing the sensors in order to avoid the increase in the size of the device, there rises a problem that projected light beams of the light-emitting elements of the sensors interfere with one another.

Therefore, an object of the present invention is to provide a sheet recognizing device and method for precisely discriminating the authentication of a sheet by performing recognition of color and watermark of a sheet and detecting the subtle characteristic of a hue ink printed on one side of the sheet.

Means for Solving Problems

The disclosure relates to sheet recognition.

Various aspects of the invention are recited in the claims.

In one aspect, a sheet recognizing device is disclosed for recognizing a sheet having a hue ink printed area in which a hue changes depending on a viewing angle.

According to some implementations, the sheet recognizing device includes a first light source for switching and projecting light of a plurality of colors at a predetermined angle to a surface of the sheet, and a second light source for switching and projecting light of a plurality of colors from a vertical direction to the surface of the sheet.

The sheet recognizing device has a first light-receiving element for receiving a light from the first light source and reflected on the surface of the sheet at the angle at which the hue of the hue ink printed area changes, and a third light source for switching and projecting light of a plurality of colors at a predetermined angle to the back of the sheet.

A second light-receiving element is for receiving a light from the third light source and reflected on the back of the sheet at the angle at which the hue of the hue ink printed area changes. A third light-receiving element is disposed on the back of the sheet so as to be opposite to the second light source.

The sheet recognizing device include first computing means for computing a first color tone depending on the hue ink printed area on the basis of each light-reception output that is output corresponding to a light-reception amount received by the first light-receiving element based on a color of light from the first light source, or on the basis of each light-reception output that is output corresponding to a light-reception amount received by the second light-receiving element based on a color of light from the third light source. Second computing means are provided for computing a second color tone independent of the hue ink printed area on the basis of each light-reception output that is output corresponding to a light-reception amount received by the first light-receiving element based on a color of light from the second light source, or on the basis of each light-reception output that is output corresponding to a light-reception amount received by the third light-receiving element based on a color of light from the third light source.

The sheet recognizing device includes sheet discriminating means for discriminating the sheet on the basis of results of the computation performed by the first computing means and the second computing means.

Also disclosed in a method of recognizing a sheet having a hue ink printed area in which hues change depending on a viewing angle Other features will be readily apparent form the following detailed description, the accompanying drawings and the claims.

Effects of the Invention

According to the sheet recognizing device and method of the present invention, light of a plurality of colors is sequentially projected to a sheet at angles at which the hues of the hue ink printed on the sheet changes, reflected light obtained when the projected light reflects on the sheet is received, light-reception outputs which are detected in response to the amount of light received are corrected at a predetermined optimum value, a ratio between the light-reception output of one color and the light-reception output of other color is computed, and the subtle characteristics of the hue ink printed on the sheet are recognized by comparing a result of the computation with a judging standard, whereby the authenticity of the sheet can be discriminated precisely.

Moreover, the sheet recognizing device comprises: the first light source for projecting light of a plurality of colors at a predetermined angle to the surface of the sheet; the second light source for projecting light of a plurality of colors from a vertical direction to the surface of the sheet; the first light-receiving element for receiving light at angles at which the hues of the reflected light in the hue ink printed area of the sheet change, the reflected light being originated from the projected light from the first light source; the third light source for projecting light of a plurality of colors at a predetermined angle to the back of the sheet; the second light-receiving element for receiving light at angles at which the hues of the reflected light in the hue ink printed area of the sheet change, the reflected light being originated from the projected light from the third light source; and the third light-receiving element which is disposed on the back of the sheet so as to be opposite to the second light source, thus the number of the light-emitting elements and light-receiving elements to be disposed can be reduced to the minimum, compared to the case in which the sensor (reflection optical sensor and transmissive optical sensor) disposing method using a known sheet recognizing method is used to detect the hue ink printed only on one side of a sheet, whereby the increase in the size of the device can be prevented.

Moreover, the number of the light-emitting elements and light-receiving elements of the sensor (light-emitting element or light-receiving element) for detecting the hue ink printed only on one side of a sheet is the minimum, thus the circuit for controlling the sensor (light-emitting element or light-receiving element) can be configured simply, whereby the cost of manufacturing the device can be made low.

In addition, even when the elements of the sensor for detecting the hue ink are limited, interference between the light-receiving elements due to emission of light-emitting elements can be prevented, compared to the case in which the sensor disposing method using the known sheet recognizing method is used.

BRIEF DESCRIPTION OF THE DRAWINGS

FIG. 3A through FIG. 3F are figures showing an example of a configuration of a bill 1 and an example of a waveform signal of light-reception data detected from the bill 1;

BEST MODE FOR CARRYING OUT THE INVENTION

Hereinafter, an embodiment of the sheet recognizing device and method according to the present invention is described in detail with reference to the attached drawings.

Figure 1:
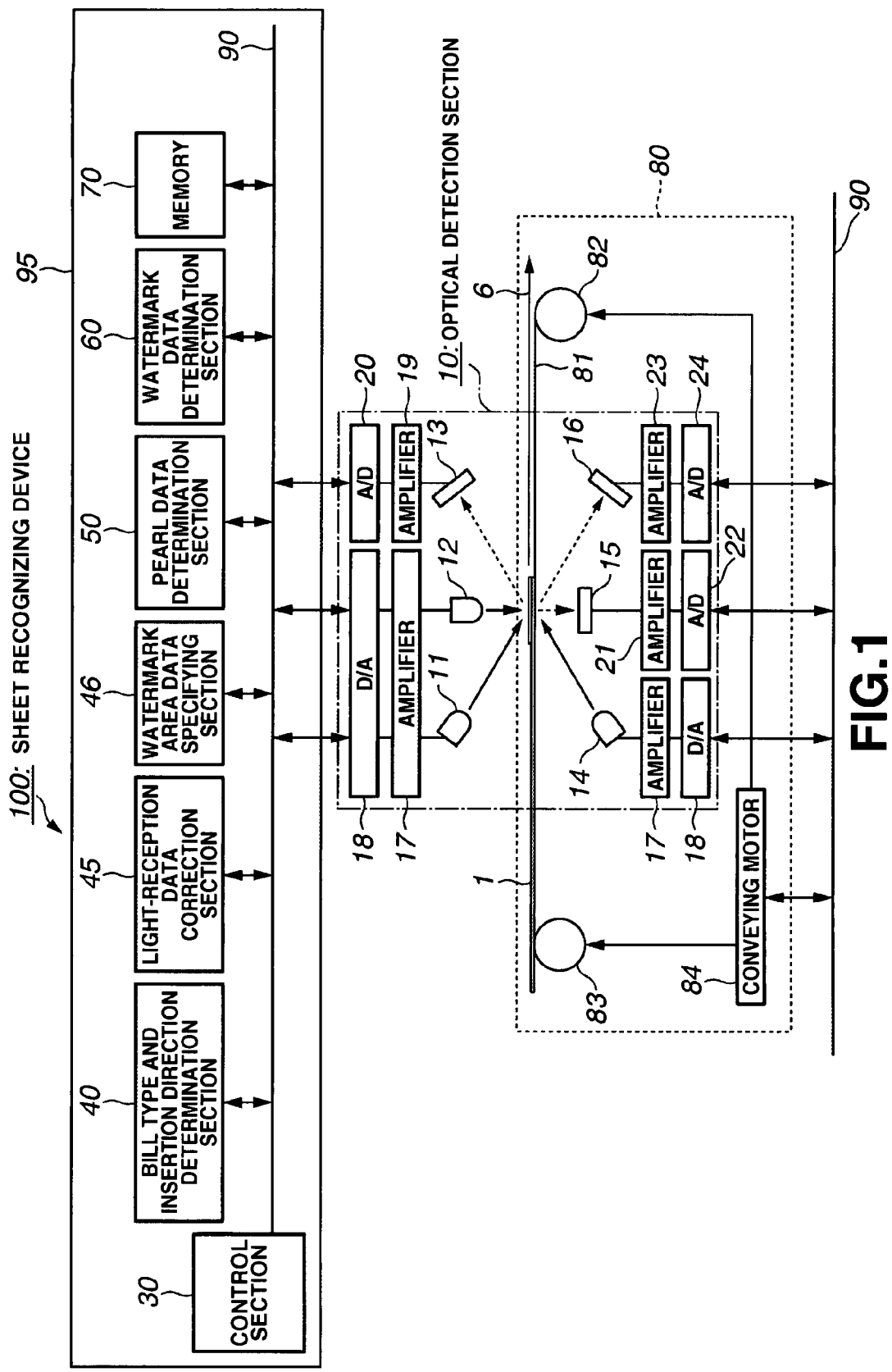
FIG. 1 is a block diagram showing a configuration example of a sheet recognizing device 100 according to the present invention.

FIG. 1 is a block diagram which schematically shows a configuration example of a substantial part of a sheet recognizing device 100 according to the present invention.

As shown in FIG. 1, the sheet recognizing device 100 is constituted by a microcomputer 95 for integrally controlling the entire sheet recognizing device 100, a bill conveying mechanism 80 (section surrounded by a dashed line) for conveying a bill 1 which is inserted from an unshown bill insertion slot of the sheet recognizing device 100, and an optical detection section 10 (section surrounded by a chain line) which sequentially projects red and green light beams on the top face (surface) and bottom face (back) of the bill 1 conveyed by the bill conveying mechanism 80, and detects light-reception output values (light-reception data) corresponding to the received amount of transmitted light obtained when the projected light transmits through the bill 1, and the received amount of reflected light reflecting at the bill 1.

It should be noted that, although not shown in FIG. 1, the sheet recognizing device 100 further comprises, in addition to the optical detection section 10, a magnetic sensor for specifying the bill type and insertion direction of the inserted bill 1 (front and back of the inserted bill 1 and forward and reverse direction of the bill 1), a transmissive optical sensor, and a reflection optical sensor. The magnetic sensor detects the magnetism of the inserted bill 1, and the transmissive optical sensor and reflection optical sensor detect light-reception outputs corresponding to the received amount of transmitted light obtained when light is projected to the inserted bill 1 and then transmits through the inserted bill 1, or the received amount of reflected light from the inserted bill 1.

The light-reception outputs of the transmitted light and reflected light, which are detected by the optical sensor, are outputted from the optical sensors respectively at predetermined time intervals at the signal levels of electric signals corresponding to the received amount of the light, sequentially stored in a predetermined storage area allocated by a continuous address in a memory 70, and temporarily stored as light-reception data at each measurement position on a scanning line of the inserted bill 1.

Further, in addition to the magnetic sensor, optical sensors, and optical detection section 10, there are disposed a start sensor for determining the position at which each of the abovementioned sensors starts measuring the inserted bill 1, and a bill insertion detection sensor for detecting that the bill 1 is inserted into the sheet recognizing device 100. The bill insertion detection sensor detects that the bill 1 is inserted into the sheet recognizing device 100, and the start sensor detects that the inserted bill 1 reaches the position at which each of the sensors starts measurement, whereby measurement of the inserted bill 1 is started by the magnetic sensor, transmissive optical sensor, reflection optical sensor, and optical detection section 10.

In the present embodiment, the sensors other than the optical detection section 10 and the bill insertion detection sensor are generically referred as to "magnetic sensor/transmitted light recognizing sensor and the like", and a known bill recognizing method performs recognition of the authentication of a bill on the basis of a result of detection performed by the magnetic sensor/transmitted light recognizing sensor and the like.

It should be noted that the explanation for the known bill recognizing method, which recognizes the authentication of a bill on the basis of a result of detection performed by the magnetic sensor/transmitted light recognizing sensor and the like, is omitted since it is not a substantial part of the sheet recognizing device 100 according to the present invention.

Furthermore, in the present embodiment, for the convenience of explanation, the transmissive optical sensor and the reflection optical sensor are provided separately from the optical detection section 10, light-reception data of transmitted light and reflected light of the inserted bill 1 may be detected for specifying the bill type and insertion direction of the inserted bill 1 by means of the optical detection section 10.

The microcomputer 95 comprises a control section 30, a bill type and insertion direction determination section 40 (bill type insertion direction discriminating means), a light-reception data correction section 45 (maximum light-reception output detecting means, correcting means), a watermark area data specifying section 46 (watermark area specifying means), pearl data determination section 50, a watermark data determination section 60, and the memory 70.

The memory 70 stores light-reception data of the reflected light and transmitted light of two colors (red, green) on the respective surfaces of the inserted bill 1, the light-reception data being detected by the optical detection section 10, light-reception data and magnetic data of the reflected light and transmitted light on the respective surface of the inserted bill 1, the light-reception data and magnetic data being detected by magnetic sensor/transmitted light recognizing sensor which are not shown, a watermark area data address reference table which is set beforehand, various reference tables such as a pearl ink printing section data address reference table, reference data thereof, and various processing programs.

It should be noted that the watermark area data address reference table is set beforehand so that address information can be referred to in accordance with the bill type and insertion direction of an authentic bill, the address information being obtained by acquiring an address of a starting point and of an end point in the storage area of the memory 70 which stores the light-reception data items of a watermark area of the authentic bill, which are detected respectively by an after-mentioned pearl light detecting sensor, non-pearl light detecting sensor, and watermark sensor of the optical detection section 10 when the authentic bill of each bill type is inserted into the sheet recognizing device 10 in forward and reverse insertion directions.

Moreover, the pearl ink printing section data address reference table is, as with the watermark area data address reference table, set beforehand so that address information can be referenced in accordance with the bill type and insertion direction of an authentic bill, the address information being obtained by acquiring an address of the starting point and of the end point in the storage area of the memory 70 which stores the light-reception data items of areas of the authentic bill on which is printed with a pearl ink, which are detected respectively by the pearl light detecting sensor and non-pearl light detecting sensor of the optical detection section 10 when the authentic bill of each bill type is inserted into the sheet recognizing device 10 in forward and reverse insertion directions.

The bill type and insertion direction determination section 40 performs a determination process for determining the bill type and insertion direction of the inserted bill 1 on the basis of the magnetic data of the inserted bill 1 which is detected by the magnetic sensor/transmitted light recognizing sensor and the like, and on the basis of the light-reception data of the transmitted light and of the reflected light.

The light-reception data correction section 45 detects the maximum light-reception amount from the amount of received red reflected light and of received green reflected light in the watermark area of the inserted bill 1, which is detected by the after-mentioned watermark area data specifying section 46 on the basis of a result of determination on the bill type and insertion direction of the inserted bill 1, the result being outputted by the bill type and insertion direction determination section 40. The light-reception data correction section 45 then corrects all of the reflected light data items of the inserted bill 1 which are detected by the optical detection section 10, on the basis of this maximum light-reception amount.

Specifically, the light-reception data correction section 45 detects the maximum light-reception amount in which the sum of the amount of received red reflected light and the amount of received green reflected light in the watermark area of the inserted bill 1 detected by the optical detection 10 is the maximum, then performs correction so that this maximum light-reception amount becomes a predetermined specified value, and then, in response to this correction, corrects all of the reflected light data items detected by the optical detection section 10.

The watermark area data specifying section 46 refers to the watermark area data address reference table on the basis of the result of determination on the bill type and insertion direction of the inserted bill 1, the result being obtained from the bill type and insertion direction determination section 40, then specifies the storage area of the memory 70 in which the light-reception data of the watermark area of the inserted bill 1 is stored, and then reads the light-reception data of the watermark area of the inserted bill 1 from the memory 70.

The pearl data determination section 50 performs authentication determination processing on the inserted bill 1, on the basis of a color tone of the ink, the pearl ink component, and the standard for judging the color tone and component, in the position of measurement on each side of the inserted bill 1, the position being obtained from the reflected light data items corrected by the light-reception data correction section 45.

It should be noted that a hue ink printed area printed with a pearl ink is formed on one side of an authentic bill which is determined as an authentic bill by the sheet recognizing device 100 of the present invention. The pearl ink in this hue ink printed area is a type of a hue ink, as described above. This pearl ink has translucent designs on which pearl luster is observed depending on the viewing angle. In this ink, when light of a specific wavelength is projected at a specific angle, it reflects in a peculiar color.

The colors of the pearl ink that changes are different depending on the type (manufacturers and the like) of the pearl ink. However, specifically, the pearl ink printed on the authentic bill in the present embodiment looks colorless (as if nothing is printed thereon) when viewing the authentic bill from a vertical direction, and looks pink when viewing from an oblique direction. In this manner the hue ink printed area is formed on one side of the authentic bill.

The inventors of the present application have performed an experiment in which light beams of different wavelengths are projected to the hue ink printed area on the authentic bill printed with the pearl ink (referred to as "pearl ink printed section" hereinafter) to measure reflected light beams obtained from the projected light beams. As a result, when projecting red light to the pearl ink printed section of the authentic bill, the amount of reflected light obtained from the projected red light was significantly large compared to other reflected light at a plain section, and, when projecting green light, the amount of reflected light at the pearl ink printed section and the other plain section were almost the same.

According to the result, the pearl data determination section 50 recognizes the color tone of the ink at the position of measurement on each side of the inserted bill 1, and precisely recognizes the pearl ink printed on the inserted bill 1, on the basis of the subtle characteristics of the pearl ink in the pearl ink printed section of the authentic bill.

The watermark data determination section 60 performs authentication determination processing on the inserted bill 1 on the basis of light-reception data of the watermark area of the inserted bill 1, which is specified by the watermark area data specifying section 46.

In the optical detection section 10, light sources 11, 12, and 14 and light-receiving elements 13, 15, and 16 are disposed on upper and lower sides perpendicular to a bill conveying path 6, with the inserted bill 1 to be conveyed by the bill conveying mechanism 80 therebetween. On the upper side perpendicular to the bill conveying path 6, when the pearl ink printed section is formed on the top face of the bill 1, there are disposed an upper light source 11 (first light source) of two-color LEDs (red, green) for projecting light from an oblique direction at a predetermined angle to the top face of the bill 1 so that the change in the hues in the pearl ink of the pearl ink printed section is the maximum, a light-receiving element 13 (first light-receiving element) opposite to the upper light source 11 so that the change in the hues of the reflected light in the pearl ink printed section on the top face of the bill 1 can be received at maximum, the reflected light being originated from the light projected by the upper light source 11, and an upper light source 12 (second light source) of the two-color LEDs (red, green) for projecting light from a vertical direction to the top face of the bill 1.

Furthermore, on the lower side perpendicular to the bill conveying path 6, when the pearl ink printed section is formed on the bottom face of the bill 1 conveyed along the bill conveying path 6, there are disposed a lower light source 14 (third light source) of two-color LEDs (red, green) for projecting light from an oblique direction at a predetermined angle to the bottom face of the bill 1 so that the change in the hues in the pearl ink of the pearl ink printed section is the maximum, a light-receiving element 16 (second light-receiving element) for receiving, at maximum, the change in the hues of the reflected light in the pearl ink printed section on the bottom face of the bill 1, the reflected light being originated from the light projected by the lower light source 14, and a light-receiving element 15 (third light-receiving element) for receiving transmitted light which is obtained when the projected light from the upper light source 12 transmits through the bill 1 at a position opposite to the upper light source 12.

The light-receiving element 15 can also receive reflected light on the bottom face of the bill 1, which is obtained from the projected light from the lower light source 14.

Regarding the means for detecting each reflected light beam on each side of the inserted bill 1, which is constituted by the light-emitting elements 11 (first light source) and 14 (third light source) each for projecting light from an oblique direction at a predetermined angle to each side of the inserted bill 1 so that the change in the hues of the pearl ink in the pearl ink printed section formed on the inserted bill 1 becomes the maximum, the light-receiving element 13 (first light-receiving element) associated with the light-emitting element 11, and the light-receiving element 16 (second light-receiving element) associated with the light-emitting element 14, the light-receiving element 13 and the light-receiving element 16 being disposed so as to receive, at maximum, the change in the hues of the reflected light in the pearl ink printed section on the each side of the inserted bill 1, the reflected light being originated from the light projected by each of the light-emitting elements 11 and 14, for the convenience of explanation, such means is referred to as "pearl light detecting sensor". The means which is constituted by the upper light source 12 (second light source) and light-receiving element 13 (first light-receiving element) or by the lower light source 14 (third light source) and light-receiving element 15 (third light-receiving element), and which detects each reflected light beam on each side of the inserted bill 1 is referred to as "non-pearl light detecting sensor" for the convenience of explanation. Further, the means which is constituted by the upper light source 12 (second light source) and light-receiving element 15 (third light-receiving element) and detects transmitted light which transmits through the inserted bill 1 is referred to as "watermark sensor" for the convenience of explanation.

Each of the light sources 11, 12, and 14 is constituted such that a D/A converter 18 converts a command signal from a digital signal to an analog signal on the basis of a command signal from the control section 30 of the microcomputer 95, and an amplifier 17 controls the fluctuation of current flowing to each of the light sources in response to the analog command signal, so that the amount of light emitted by each of the light sources can be adjusted.

The light-receiving elements 13, 15, and 16 are light-receiving elements such as photodiodes, wherein an electric signal, which is outputted at a signal level corresponding to the received amount of reflected light or transmitted light received by each of the light-receiving elements, is amplified by amplifiers 19, 21, and 23 corresponding to the light-receiving elements 13, 15, and 16 respectively, converted into a digital signal by each of A/D converters 20, 22, and 24 corresponding to each of the amplifiers 19, 21, and 23, and then stored in a predetermined storage area of the memory 70 via a bus 90.

It should be noted that an optical wavelength and any wavelength of an infrared ray and an ultraviolet ray can be applied to the light-receiving element 15, and the light-emitting element 12 is replaced with a device from which each wavelength can be transmitted that corresponds to each wavelength applied to the light-receiving element 15.

The bill conveying mechanism 80 comprises a conveying belt 81 for conveying the bill 1 inserted from the bill insertion slot, rollers 82 and 83 which support the conveying belt 81, and a conveying motor 84 which can drive the roller 82 or 83 a desired number of rotations in a desired rotation direction at a desired rotation speed, and move the conveying belt 81 by a desired conveying distance in a desired direction at a desired conveying speed.

It should be noted that the conveying motor 84 performs control of the drive of the roller 82 or 83 on the basis of the command signal from the control section 30.

Reception of data signals, control signals and the like between the sections of the sheet recognizing device 100 is performed on the basis of the command signals from the control section 30 of the microcomputer 95 via the bus 90, and the control section 30 integrally controls the entirety.

Figure 2:
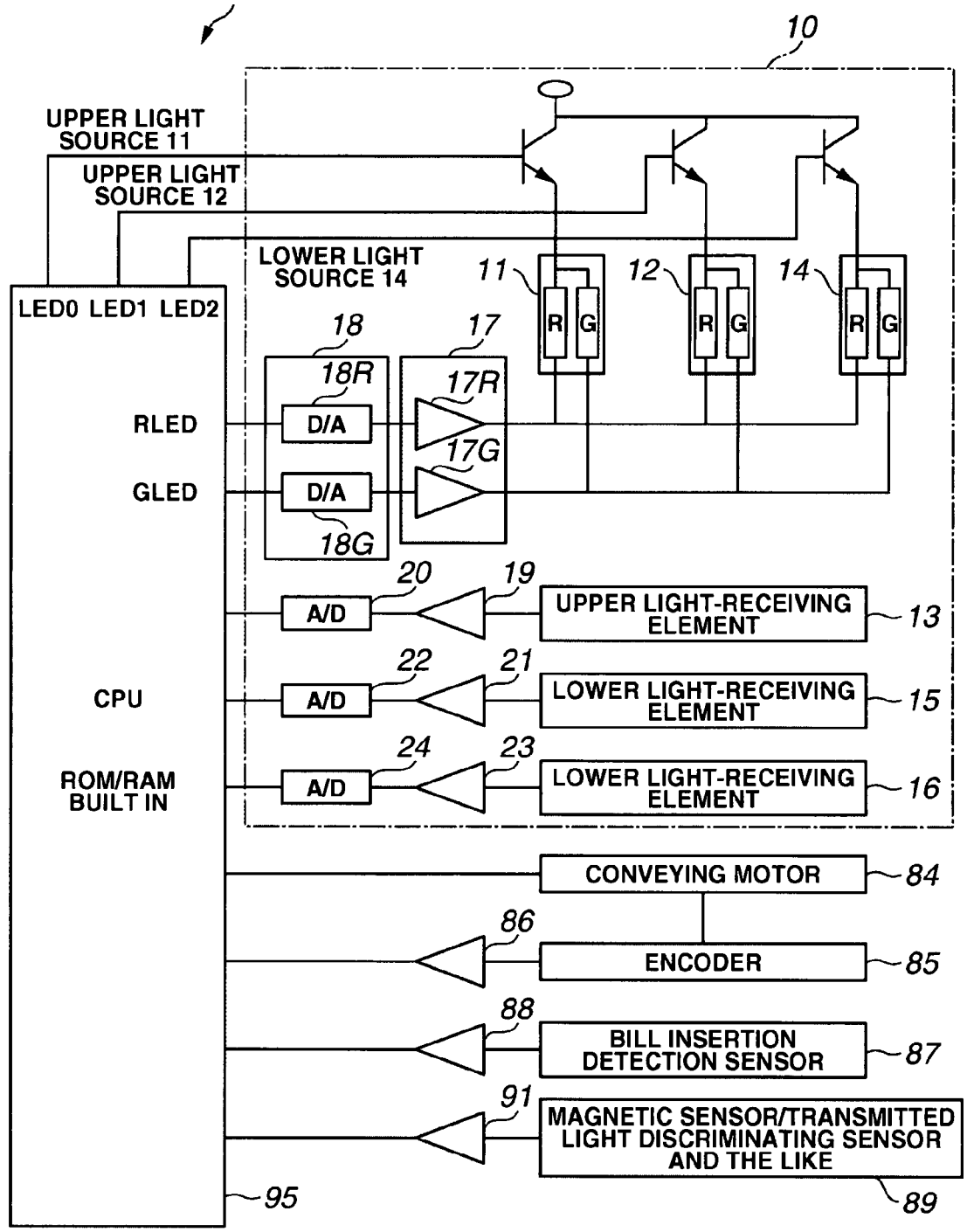
FIG. 2 is a circuit block diagram showing an example of a circuit configuration of the sheet recognizing device 100.

In addition to the configuration diagram of the sheet recognizing device 100 shown in FIG. 1, a schematic diagram of a circuit configuration of the sheet recognizing device 100 is shown in FIG. 2 in order to further clarify the process operations of the sheet recognizing device 100.

FIG. 2 is a circuit block diagram which schematically shows an example of a circuit configuration of the sheet recognizing device 100. As shown in FIG. 2, in the optical detection section 10 (section surrounded by a chain line), the upper light sources 11, 12 of the two-color LEDs (red (R) and green (G)) are disposed on the upper side perpendicular to the bill conveying path 6 and the lower light source 14 of the two-color LEDs (red (R) and green (G)) is disposed on the lower side perpendicular to the bill conveying path 6. The two-color LEDs (red, green) of the light sources are connected to the microcomputer 95 via the D/A converter 18 capable of controlling the fluctuation of current flowing to the LED of each color and via the amplifier circuit 17.

Further, the D/A converter 18 and amplifier circuit 17 are constituted by, for the LEDs of the corresponding colors, a D/A converter 18R (corresponding to the red LED), a D/A converter 18G (corresponding to the green LED), an amplifier circuit 17R (corresponding to the red LED), and an amplifier circuit 17G (corresponding to the green LED).

It should be noted that a prism or lens for polarizing the projection angle can be disposed in each of the light sources and light-emitting elements.

The light-receiving element 13 is connected to the microcomputer 95 via the A/D converter 20 and the amplifier circuit 19, the light-receiving element 15 is connected to the microcomputer 95 via the A/D converter 22 and the amplifier circuit 21, and the light-receiving element 16 is connected to the microcomputer 95 via the A/D converter 24 and the amplifier circuit 23.

Each of the light-receiving elements 13, 15 and 16 outputs an electric signal corresponding to the amount of received reflected light and the amount of received transmitted light. The electric signal outputted from each of the light-receiving element is amplified by each of the amplifiers 19, 21, and 23 corresponding to each of the light-receiving elements, is then converted into a digital signal by each of the A/D converters 20, 22, and 24 corresponding to each amplifier 19, 21, and 23, and is stored in the memory 70 of the microcomputer 95.

Moreover, the conveying motor 84 for performing conveyance direction on the inserted bill 1 is connected to the microcomputer 95, and performs drive control on the roller 82 or 83 of the bill conveying mechanism 80 on the basis of the command signals transmitted from the control section 30 of the microcomputer 95.

An encoder 85 is connected to the conveying motor 84, and also connected to the microcomputer 95 via an amplifier circuit 86. The encoder 85 amplifies a pulse signal encoded in response to drive of the conveying motor 84, at the amplifier circuit 86, and outputs the pulse signal to the microcomputer 95.

A bill insertion detection sensor 87 is connected to the microcomputer 95 via an amplifier circuit 88, detects the bill 1 inserted into the sheet recognizing device 100, amplifies a detected signal at the amplifier circuit 88, and output the detected signal to the microcomputer 95.

In the sheet recognizing device 100, as described above, the magnetic sensor for detecting the magnetism of the inserted bill 1, the transmissive optical sensor for detecting transmitted light originated from the light projected to the inserted bill 1, and the magnetic sensor/transmitted light recognizing sensor and the like 89 indicating the reflected light sensor for detecting reflected light originated from the light projected to the inserted bill 1 are connected to the microcomputer 95 via an amplifier circuit 91. The magnetic data or light-reception data which is detected by each of the sensors are amplified by the amplifier circuit 91 and inputted to the microcomputer 95.

The authentication of the inserted bill 1 can be recognized by means of the known bill recognizing method and the magnetic data or light-reception data which is detected from the inserted bill 1 by the plurality of sensors such as the magnetic sensor/transmitted light recognizing sensor and the like 89.

It should be noted that explanation of the known bill recognizing method using the magnetic sensor/transmitted light recognizing sensor and the like 89 is omitted since it is not a substantial part of the sheet recognizing device 100 according to the present invention.

A method of precisely discriminating the authenticity of a sheet inserted into the sheet recognizing device 100 configured in the manner described above is described simply with reference to the configuration of an authentic bill according to the present invention.

FIG. 3A through FIG. 3F are figures showing a schematic configuration of an authentic bill 2 which is recognized as an authentic bill by the sheet recognizing device 100, and an example of a signal (waveform) corresponding to each light-reception data item of the authentic bill 2 which is detected by each sensor of the optical detection section 10.

In FIG. 3A through FIG. 3F, FIG. 3A is a figure showing a configuration example of the authentic bill 2, FIG. 3B is a figure showing a waveform signal of reflected light of each color (red, green) of the authentic bill 2, the reflected light being detected by the pearl light detecting sensor, FIG. 3C is a figure showing a waveform signal of a ratio of the green reflected light to the red reflected light shown in FIG. 3B, FIG. 3D is a figure showing a waveform signal of the reflected light of each color (red, green) of the authentic bill 2, the reflected light being detected by the non-pearl light detecting sensor, FIG. 3E is a figure showing a waveform signal of a ratio of the green reflected light to the red reflected light shown in FIG. 3D, and FIG. 3F is a figure showing a waveform of a ratio between the ratio of the green reflected light to the red reflected light detected by the non-pearl light detecting sensor shown in FIG. 3E, and the ratio of the green reflected light to the red reflected light detected by the pearl light detecting sensor shown in FIG. 3C.

As shown in FIG. 3A, a watermark area 5 is formed in the authentic bill 2, pearl ink printed sections 3, 4 are formed on each end in a longitudinal direction of the authentic bill 2, and the authentic bill 2 is conveyed by the bill conveying mechanism 80 along the bill conveying path 6 in a predetermined conveyance direction (direction of the arrow shown in the figure).

It should be noted that the pearl ink printed sections 3, 4 are printed only on one side of the authentic bill 2.

When the authentic bill 2 is conveyed into the optical detection section 10 along the bill conveying path 6, the amount of received two-color (red, green) reflected light or two-color (red, green) transmitted light at the position of measurement on each side of the authentic bill 2 is measured on the basis of the command signals from the control section 30 of the microcomputer 95, the reflected light or transmitted light being originated from the light sources 11, 12, 14 and the light-receiving elements 13, 15, 16 which are disposed inside the optical detection section 10. Then, the light-reception data for the reflected light data or transmitted light data of a received light output value corresponding to each amount of light received is collected.

The two-color (red, green) LEDS of the upper light source 11 or lower light source 14 are caused to emit light beams sequentially to the inserted authentic bill 2. When the reflected light of each color from the authentic bill 2 is received by the light-receiving element 13 or 16, that is, when the reflected light on each side of the inserted authentic bill 2 is received by the pearl light detecting sensor, a light-reception output corresponding to the amount of received red reflected light is detected as a waveform signal shown by item 101 in FIG. 3B, and a light-reception output corresponding to the amount of received green reflected light is detected as a waveform signal shown by item 102 in FIG. 3B, whereby the ratio of the light-reception output of the green reflected light to the light-reception output of the red reflected light (referred to as "red-green ratio (oblique light beam)" hereinafter) is computed as a waveform signal 103 as shown in FIG. 3C, the red and green reflected light being received by the pearl light detecting sensor.

It should be noted that information on a color tone (first color tone) depending on the pearl ink of the pearl ink printed sections 3, 4 can be obtained from the red-green ratio (oblique light beam) based on the light-reception data of the inserted authentic bill 2 obtained from the pearl light detecting sensor.

Specifically, the characteristics of the pearl ink on the authentic bill 2 are apparent in the red-green ratio (oblique light beam) based on the light-reception data obtained from the pearl light detecting sensor, the characteristics of the pearl ink being such that the amount of the red reflected light at the pearl ink printed sections 3, 4 of the authentic bill 2 is significantly larger than the amount of red reflected light at other plain section, the former red reflected light being originated from the projected red light, while the amount of the green reflected light at the pearl ink printed sections 3, 4 of the authentic bill 2 is almost the same as the amount of the green reflected light at the plain section other than the pearl ink printed sections 3, 4, the green reflected light being originated from the projected green light.

Specifically, as shown in FIGS. 3A and 3B, a value of the light-reception output of the red reflected light of the inserted authentic bill 2, the red reflected light being originated from the projected red light of the pearl light detecting sensor, is detected as a value larger at the pearl ink printed sections 3, 4 of the authentic bill 2 than in a plain section of the watermark area 5. In an other section, in accordance with the color of a design printed on the authentic bill 2, the light-reception output is large in a red printed area and smaller in a black printed area, thus light-reception outputs which are different in accordance with the colors are obtained.

Further, the light-reception output of the green reflected light of the inserted authentic bill 2 is almost the same with respect to the pearl ink printed sections 3, 4 and other plain section, the green reflected light being originated from the projected green light of the pearl light detecting sensor, and the light-reception output of the green reflected light at the pearl ink printed sections 3, 4 is smaller than the light-reception output of the red reflected light.

Moreover, in an other section, the light-reception output is large at a green printed area and small at a black printed area in accordance with the color of a design printed on the authentic bill 2, thus light-reception outputs which are different in accordance with the colors are obtained.

It should be noted in FIG. 3B through FIG. 3E that the signal (waveform) of the light-reception output detected at a section in which a design on the authentic bill 2 is printed changes in response to the change in color of the design printed on the authentic bill 2. However, this printed section is not a substantial part of the present invention, thus the detailed explanation of the signal waveform of the light-reception output in this section where the design on the authentic bill 2 is printed is omitted, but is instead shown as a rectangular hatching design for the convenience of explanation.

When computing the ratio of the light-reception output of the green reflected light to the light-reception output of the red reflected light (red-green ratio (oblique light beam)) of the authentic bill 2, the red and green reflected light being detected from the pearl light detecting sensor, information of the color tone (first color tone) depending on the pearl ink in which the value of the ratio in the pearl ink printed sections 3,4 of the authentic bill 2 is smaller than the value in the plain section of the watermark area 5 can be obtained, as shown in FIGS. 3A and 3C.

When the reflected light on each side of the authentic bill 2, which is obtained from the non-pearl light detecting sensor is received with respect to the inserted authentic bill 2, that is, when the two-color (red, green) LEDs of the upper light source 12 are caused to emit light sequentially to the authentic bill 2 and the light is received at the light-receiving element 13, or when the two-color (red, green) LEDs of the lower light source 14 are caused to emit light sequentially and the light is received at the light-receiving element 15, a light-reception output of the red reflected light is detected as a waveform signal as shown by item 104 in FIG. 3D, and a light-reception output of the green reflected light is detected as a waveform signal as shown by item 105 in FIG. 3D, whereby the ratio of the light-reception output of the green reflected light to the light-reception output of the red reflected light (referred to as "red-green ratio (vertical light beam)" hereinafter) is computed as a waveform signal 106 as shown in FIG. 3E, the red and green reflected light being received by the non-pearl light detecting sensor.

It should be noted that information on a color tone (second color tone) independent of the pearl ink of the pearl ink printed sections 3, 4 can be obtained from the red-green ratio (vertical light beam) based on the reflected light data of the inserted authentic bill 2 obtained from the non-pearl light detecting sensor.

Specifically, as shown in FIGS. 3A and 3D, when the red light and the green light of the non-pearl light detecting sensor are sequentially emitted and projected to the authentic bill 2, and the light-reception outputs from the reflected lights are sequentially detected, the light-reception outputs of the pearl ink printed sections 3, 4 of the authentic bill 2 are almost the same as the plain section of the watermark area 5. In an other section, the light-reception outputs are large at a printed area of a color corresponding to an emission color of the two-color (red, green) LEDs and small at a black printed area in accordance with the color of a design printed on the authentic bill 2, thus the light-reception outputs which are different in accordance with the colors are obtained.

The information of the color tone (second color tone) independent of the pearl ink can be obtained, the information indicating that the ratio of the light-reception output of the green reflected light to the light-reception output of the red reflected light (red-green ratio (vertical light beam)) obtained from the non-pearl light detecting sensor does not much change in the pearl ink printed sections 3, 4 and the plain section of the watermark area 5 as shown in FIGS. 3A and 3E.

When computing the ratio of the red-green ratio (oblique light beam) obtained from the pearl light detecting sensor shown in FIG. 3C to the red-green ratio (vertical light beam) obtained from the non-pearl light detecting sensor shown in FIG. 3E (referred to as "ratio between red-green ratios" hereinafter), the pearl ink printed sections 3, 4 of the authentic bill 2 with a significant difference as indicated with 107-a, 107-b of FIG. 3F are detected, compared to other areas (the watermark area and an area printed with designs).

According to these facts, in the sheet recognizing device 100 of the present invention, by computing the red-green ratio (oblique light beam) based on the light-reception output of the reflected light of the inserted bill 1, the light-reception output being detected by the above-mentioned pearl light detecting sensor, the information containing the color tone (first color tone) depending on the pearl ink of the pearl ink printed sections 3, 4 printed on the authentic bill 2 is obtained. By computing the red-green ratio (vertical light beam) based on the light-reception output of the reflected light of the inserted bill 1, the light-reception output being detected by the non-pearl light detecting sensor, the information containing the color tone (second color tone) independent of the pearl ink of the pearl ink printed sections 3, 4 printed on the authentic bill 2 is obtained. By computing the ratio (ratio between red-green ratios) between the red-green ratio (vertical light beam) based on the light-reception output of the reflected light of the inserted bill 1, the light-reception output being detected by the non-pearl light detecting sensor, and the red-green ratio (oblique light beam) based on the light-reception output of the reflected light of the inserted bill 1, the light-reception output being detected by the above-mentioned pearl light detecting sensor, the subtle characteristics of the pearl ink of the pearl ink printed sections 3, 4 printed on the authentic bill 2 are detected. Unlike a simple method of discriminating a hue ink by means of the light-reception output of individual reflection optical sensors, in this device, further precise discrimination of the authenticity of the bill is performed on the basis of a result of discrimination of the subtle characteristics of the pearl ink printed on the bill.

A process operation performed by the sheet recognizing device 100 for precisely discriminating the authentication of the inserted bill 1 is described in detail with reference to the flowcharts shown from FIG. 4 through FIG. 12.

Figure 4:
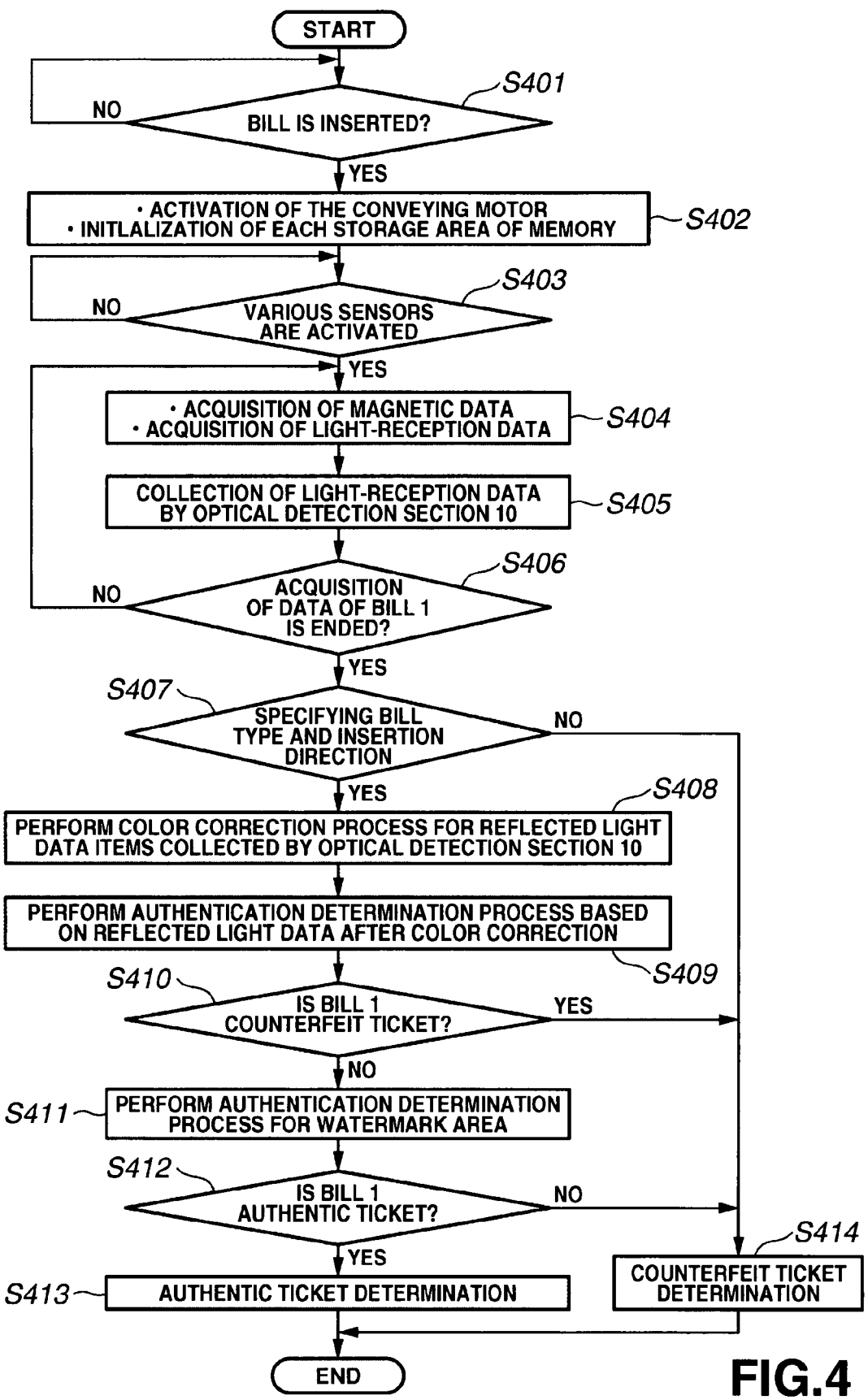
FIG. 4 is a main flowchart showing a process operation in which the sheet recognizing device 100 recognizes the authentication of the inserted bill 1.

FIG. 4 is a main flowchart showing a process operation in which the sheet recognizing device 100 recognizes the authentication of the inserted bill 1.

As shown in the flowchart of FIG. 4, when the bill insertion detection sensor 87 detects that the bill 1 is inserted from the unshown bill insertion slot of the sheet recognizing device 100 (YES in step S401), the conveying motor 84 performs control drive of the roller 82 or 83 supporting the conveying belt 81 on the basis of the command signal from the control section 30 of the microcomputer 95, the inserted bill 1 is conveyed along the bill conveying path 6, and each storage area in the memory 70 for storing the magnetic data and light-reception data is initialized, the magnetic data and light-reception data being detected from the inserted bill 1 by each sensor of the optical detection section 10, such as the magnetic sensor/transmitted light recognizing sensor and the like 89 (step S402).

The storage areas (the detail thereof is described hereinafter) for storing the magnetic data and light-reception data of the inserted bill 1, which are detected by the magnetic sensor/transmitted light recognizing sensor and the light 89 and the optical detection section 10 such as disposed at a predetermined position of the bill conveying path 6, are allocated in the memory 70. When each of these storage areas is initialized, each of the sensors of the magnetic sensor/transmitted light recognizing sensor and the light 89 and the optical detection section 10 is operated (YES in step S403), and the magnetic data and light-reception data (reflected light data and transmitted light data) of the inserted bill 1 which are detected by each of the sensors are sequentially stored in a predetermined storage area of the memory 70 (step S404, step S405).

Collection of the data from the inserted bill 1, which is performed by the magnetic sensor/transmitted light recognizing sensor and the like 89, is performed in the same was as in a detection and collection method in the prior art.

The optical detection section 10 sequentially projects light beams of two colors, red light and green light, from an oblique direction or vertical direction at a predetermined angle to each side of the bill 1 at the positions of measurement on the top face and bottom face of the conveyed bill 1, on the basis of the command signal from the control section 30 of the microcomputer 95. The optical detection section 10 then receives reflected light obtained when each of the projected light beams reflects on each side of the bill 1 or transmitted light when each of the projected light beams transmits through the bill 1, and sequentially stores thus obtained light-reception output values corresponding to the amounts of the received light beams, as light-reception data (reflected light data, transmitted light data), in the predetermined storage area of the memory 70.

It should be noted that collection of the light-reception data of the inserted bill 1, which is performed by the optical detection section 10, is performed simultaneously with data collection of the magnetic sensor/transmitted light recognizing sensor and the like 89.

Furthermore, each of the sensors of the optical detection section 10 can be used as light-reception data detecting means of the inserted bill 1 for determining the bill type and insertion direction of the inserted bill 1.

The detail of the process operation of "collecting the light-reception data of the inserted bill 1 which is performed by the optical detection section 10" in the step S405 is described hereinafter.

When each data item is detected by each sensor at the position of measurement on the inserted bill 1 and sequentially stored in each storage area of the memory 70, and data collection for one inserted bill 1 is ended (YES in step S406), the bill type and insertion direction determination section 40 of the microcomputer 95 specifies the front and back, forward and reverse insertion directions, and the bill type of the inserted bill 1 on the basis of the magnetic data and the light-reception data of the transmitted light and reflected light, which are detected by the magnetic sensor/transmitted light recognizing sensor and the like 89, and outputs a result (YES in step S407).

In the step S407, when the bill type or insertion direction cannot be specified on the basis of each data detected by the magnetic sensor/transmitted light recognizing sensor and the like 89, that is, when the magnetic data and the light-reception data for the transmitted light or reflected light, which are detected by the magnetic sensor/transmitted light recognizing sensor and the like 89 in accordance with the bill type and insertion direction of an authentic bill, do not previously match the magnetic data and the light-reception data for the transmitted light or reflected light, which are detected from the inserted bill 1 (NO in the step S407), the inserted bill 1 is determined as a counterfeit ticket (step S414).

It should be noted that magnetic data and the light-reception data for the transmitted light or reflected light, which are detected by the magnetic sensor/transmitted light recognizing sensor and the like 89 in accordance with the bill type and insertion direction of the authentic bill, are stored beforehand as reference data in the predetermined storage area of the memory 70, and the bill type and insertion direction determination section 40 refers to the reference data to specify the bill type and insertion direction of the inserted bill 1.

In the step S407, when the bill type and insertion direction of the inserted bill 1 are specified, the light-reception data correction section 45 performs color correction processing for all of the reflected light data items, which are collected by the optical detection section 10, on the basis of the specified reflected light data of the watermark area of the inserted bill 1 which is obtained in accordance with the specified bill type and insertion direction of the inserted bill 1 (step S408).

It should be noted that the reflected light data of the watermark area of the inserted bill 1 is read from the memory 70 after the watermark area data specifying section 46 refers to the watermark area data address reference table and the bill type and insertion direction of the inserted bill 1 which is determined and outputted by the bill type and insertion direction determination section 40.

This color correction is performed for the light-reception output values of all of the reflected light data items collected by the optical detection section 10, in order to constrain variation of recognition and determination due to variation of the amount of emitted light or the light-reception sensitivity, which is caused by time degradation of the light sources 11, 12, 14 and light-receiving elements 13, 15, 16 of the optical detection section 10, or variation of the amount of emitted light or the light-reception sensitivity, which is caused by change in the ambient temperature or dust adhered to the light sources and light-receiving elements. It should be noted that the detail of "color correction processing for the reflected light data items collected by the optical detection section 10" in the step S408 is described hereinafter.

When all of the reflected light data items collected by the optical detection section 10 are subjected to color correction by the light-reception data correction section 45, the pearl data determination section 50 determines whether the inserted bill 1 is a counterfeit ticket or not, on the basis of the reflected light data items which are subjected to color correction (color-corrected data items) (step S409).

Specifically, the pearl data determination section 50 determines whether the inserted bill 1 is a counterfeit ticket or not, on the basis of the color tone and pearl ink component of the ink at the position of measurement on each side of the inserted bill 1, which are obtained from the color-corrected data, and on the basis of the judging standard therefore, and determines whether the inserted bill 1 is a counterfeit ticket (YES in step S410) or not (NO in the step S410).

It should be noted that the detail of "authentication determination processing based on the reflected light data after color correction", which is performed by the pearl data determination section 50 in the step S409, is described hereinafter.

When it is determined that the inserted bill 1 is not a counterfeit ticket (NO in the step S410), the watermark data determination section 60 performs determination processing on whether the inserted bill 1 is an authentic bill or not, on the basis of the light-reception data (reflected light data, transmitted light data) of the watermark area of the inserted bill 1 (step S411), judges the inserted bill 1 as an authentic bill (YES in step S412, step S413) or a counterfeit ticket (NO in the step S412, step S414), and ends the processing.

It should be noted that the detail of "authentication determination processing for the watermark area", which is performed by the watermark data determination section 60 in the step S411, is described hereinafter.

Here, the above-described operation of "processing of collecting the light-reception data of the inserted bill 1 which is performed by the optical detection section 10" in the step S405 is described in detail with reference to FIG. 5 through FIG. 8. The detail of the "color correction processing for the reflected light data items collected by the optical detection section 10", which is performed by the light-reception data correction section 45 in the step S408, is described with reference to FIG. 9. The detail of the "authentication determination processing based on the reflected light data after color correction", which is performed by the pearl data determination section 50 in the step S409, is described with reference to FIG. 10 and FIG. 11. The detail of the "authentication determination processing for the watermark area", which is performed by the watermark data determination section 60 in the step S411, is described with reference to FIG. 12.

Figure 5:
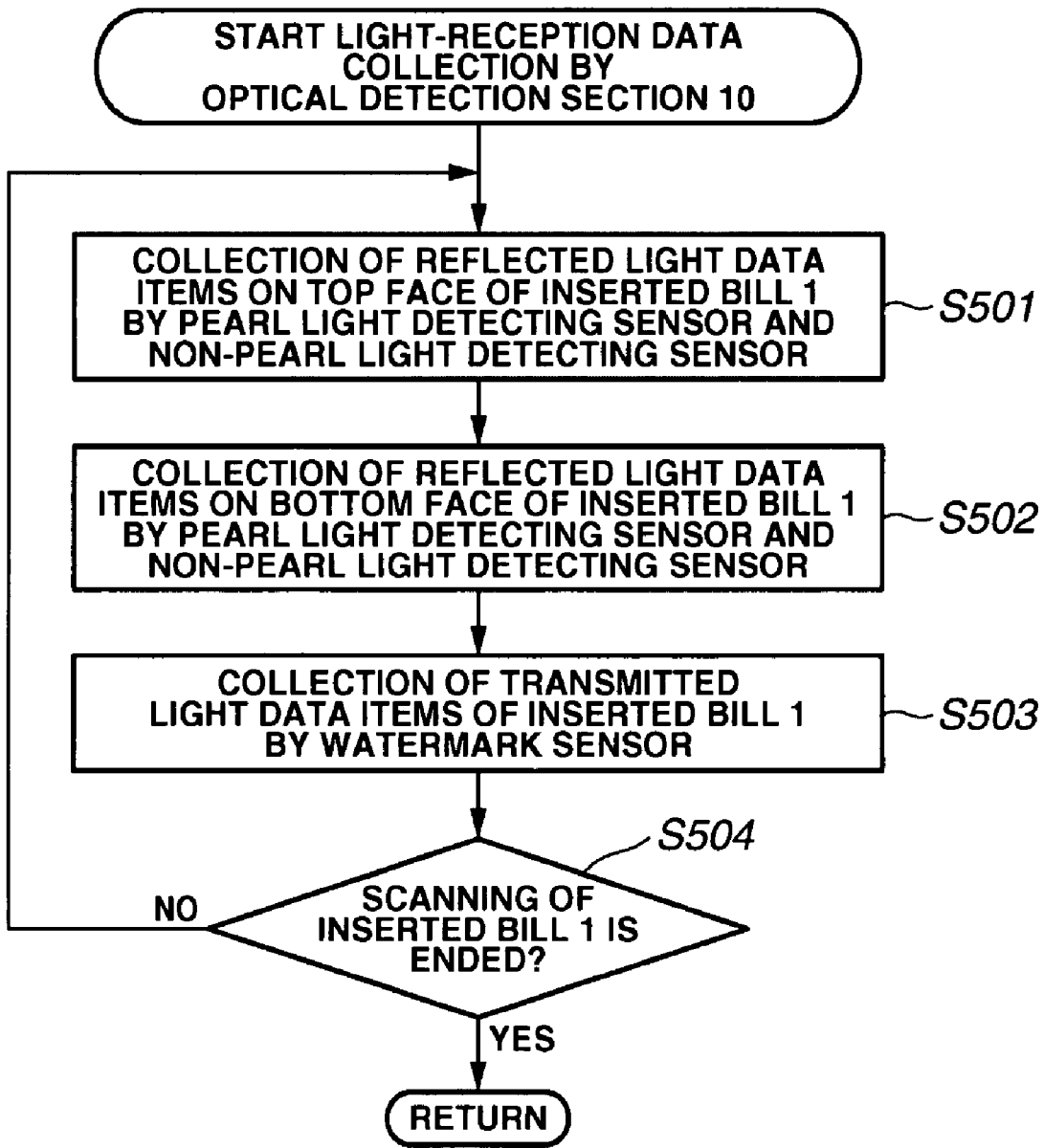
FIG. 5 is a main flowchart showing a process operation for collecting the light-reception data of the inserted bill 1 by means of an optical detection section 10.
Figure 6:
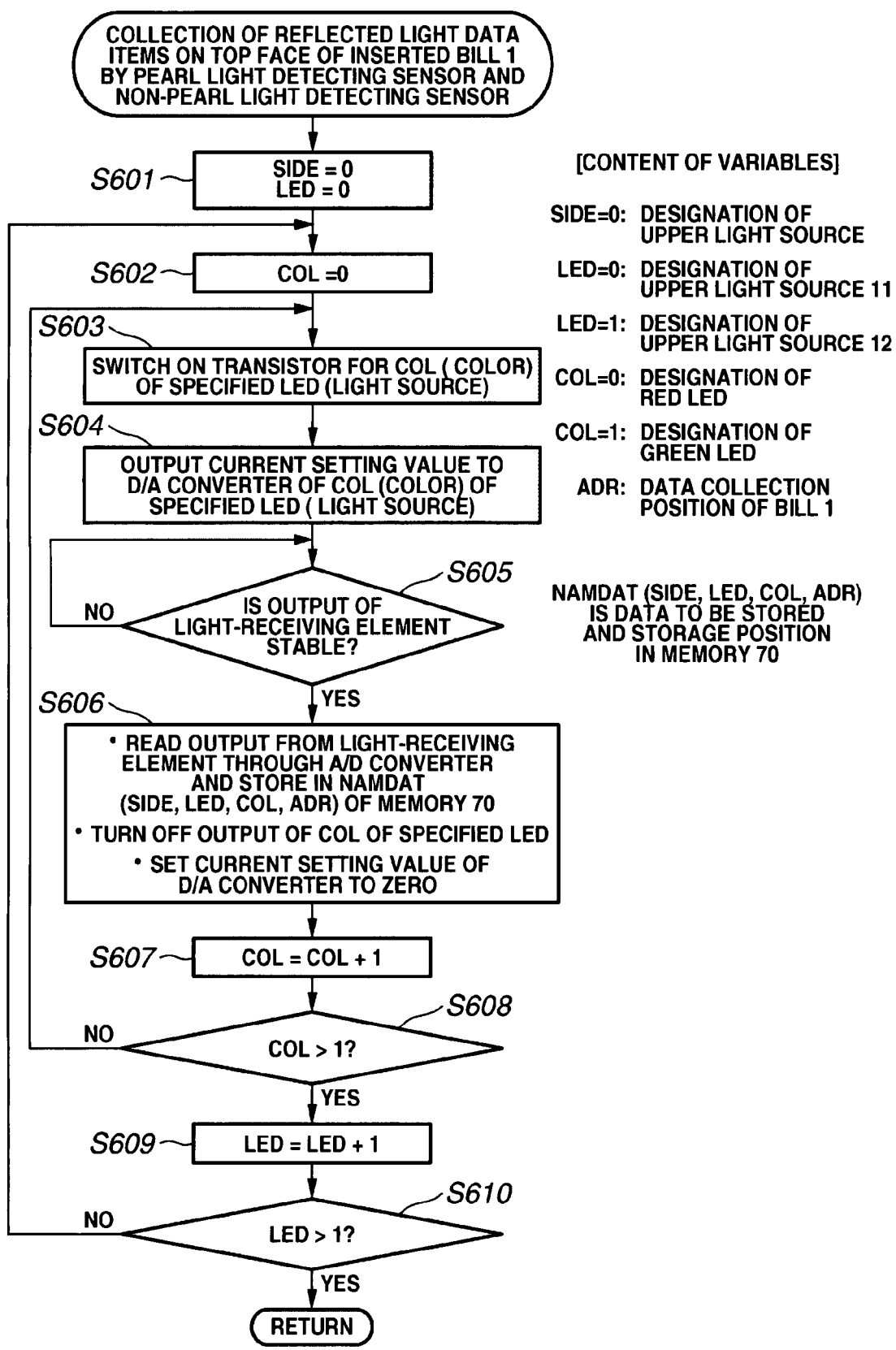
FIG. 6 is a flowchart showing a process operation for collecting data of reflected light on the top face of the inserted bill 1 by means of a pearl light detecting sensor and a non-pearl light detecting sensor.
Figure 7:
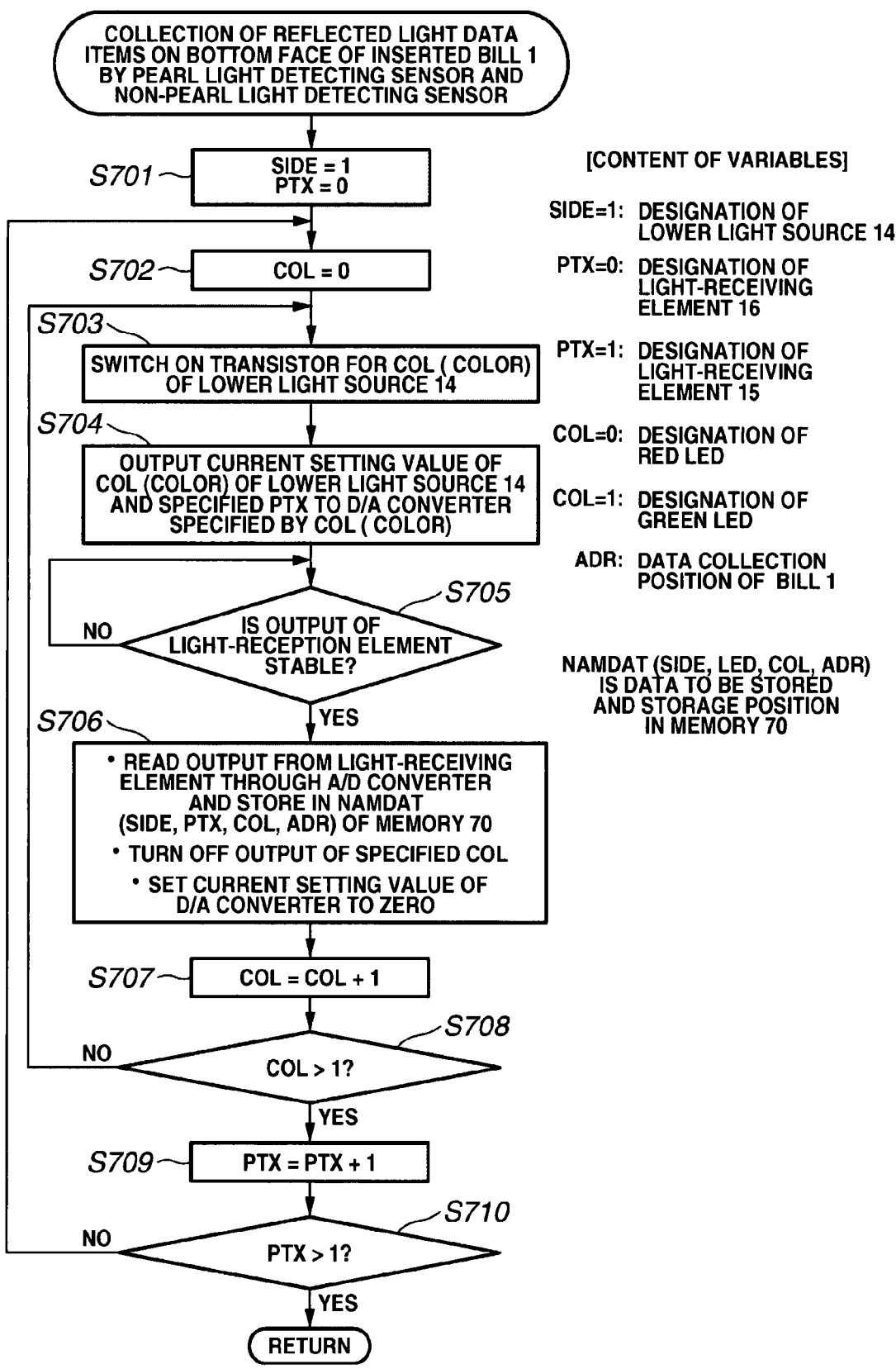
FIG. 7 is a flowchart showing a process operation for collecting data of reflected light on the bottom face of the inserted bill 1 by means of the pearl light detecting sensor and the non-pearl light detecting sensor.
Figure 8:
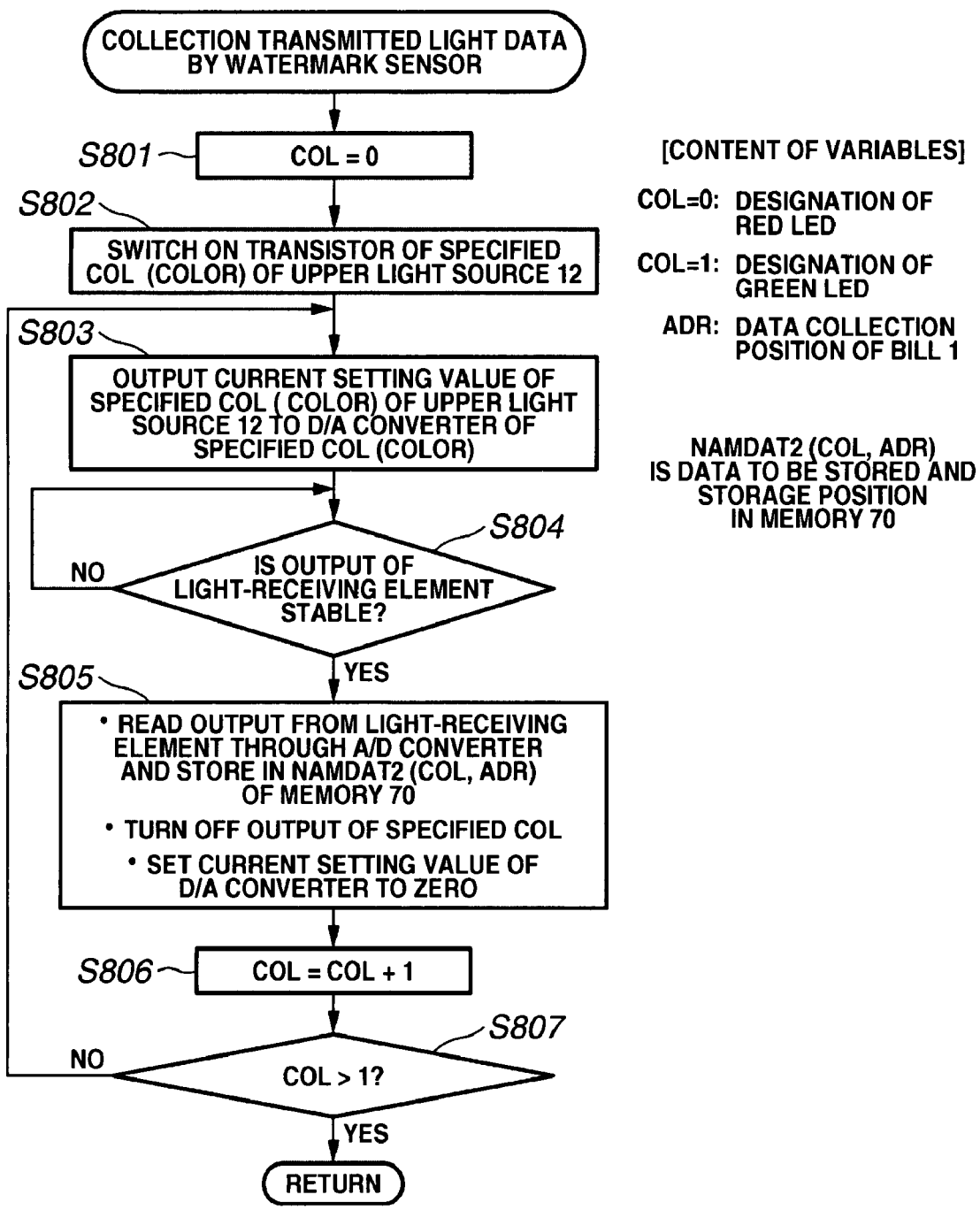
FIG. 8 is a flowchart showing a process operation for collecting transmissive light data of the inserted bill 1.

FIG. 5 is a schematic flowchart showing an operation of collecting the light-reception data, which is performed by the optical detection section 10 on the basis of the command signal from the control section 30 of the microcomputer 95. FIG. 6 through FIG. 8 are flowcharts showing the detail of the process operation of each step in the schematic flowchart of FIG. 5.

As shown in the flowchart of FIG. 5, the process operation of collecting the light-reception data (reflected light data, transmitted light data) from the optical detection section 10 at the position of measurement on each side of the inserted bill 1 is carried out sequentially from the measurement starting position to the measurement ending position of the inserted bill 1 in the order of collecting each reflected light data item of the two colors (red, green) detected by the pearl light detecting sensor and non-pearl detecting sensor on the top face of the inserted bill 1 (step S501), collecting each reflected light data item of the two colors (red, green) detected by the pearl light detecting sensor and non-pearl light detecting sensor on the bottom face of the inserted bill 1 (step S502), and collecting each transmitted light data item of the two colors (red, green) detected by the watermark sensor (step S503). When the inserted bill 1 passes through the optical detection section 10 (YES in step S504), the data collection processing performed by the optical detection section 10 for one inserted bill 1 is ended.

In the process operation of "collection of the reflected light data item on the top face of the inserted bill 1, which is performed by the pearl light detecting sensor and non-pearl detecting sensor" in the step S501, specifically, the two-color (red, green) LEDs of the upper light source 11 are sequentially caused to emit light, and data items of light-reception output values corresponding to the amount of reflected light of each color on the top face of the inserted bill 1 are collected, the reflected light being received by the light-receiving element 13. Next, the two-color (red, green) LEDs of the upper light source 12 are sequentially caused to emit light, and data items of light-reception output values corresponding to the amount of reflected light of each color on the top face of the inserted bill 1 are collected, the reflected light being received by the light-receiving element 13.

Specifically, as shown in the flowchart of FIG. 6, the control section 30 of the microcomputer 95 turns ON a transistor of the red LED of the upper light source 11 in accordance with each position of measurement on the inserted bill 1 (steps S601, 602, 603), outputs a current setting value to the D/A converter 18R of the red LED (see FIG. 2), and causes the red LED of the upper light source 11 to emit light (step S604). After the light-reception output of the light-receiving element 13 is stabilized (YES in step S605), a light-reception output signal, which is outputted from the light-receiving element 13 in response to the reflected light on the top face of the inserted bill 1, is amplified by the amplifier circuit 19, is converted into digital reflected light data by the A/D converter 20, and is stored in the predetermined storage area of the memory 70 of the microcomputer 95.

The predetermined storage area of the memory 70 in which is stored the red reflected light data of the top face of the inserted bill 1, which is obtained from the pearl light detecting sensor, is a storage area associated with NAMDAT (SIDE, LED, COL, ADR). With regard to each variable of the NAMDAT (SIDE, LED, COL, ADR), SIDE is managed as a value "0" indicating the upper light source and a value "1" indicating the lower light source, LED is managed as a value "0" indicating the upper light source 11 and a value "1" indicating the upper light source 12, COL is managed as a value "0" indicating the red LED and a value "1" indicating the green LED, and ADR is managed as a value indicating information on the data collection position of the inserted bill 1. The reflected light data on the top face of the inserted bill 1 which is obtained by the red LED emission at the upper light source 11 is stored in a storage area where SIDE=0, LED=0, COL=0, and ADR=n (n is a value corresponding to the measurement position between 0 of the measurement starting position and the n of the measurement ending position).

When collection of the reflected light data items at the measurement position on the top face of the bill 1 is ended, the reflected light data being obtained from the red LED emission at the upper light source 11, the transistor of the red LED of the upper light source 11 is turned OFF, the current setting value of the D/A converter 18R of the red LED is set to 0 (step S606), the green LED of the upper light source 11 is caused to emit light, and the light-reception output signals, which are outputted from the light-receiving element 13 in response to the reflected light on the top face of the inserted bill 1 in the same manner as described above, are stored in the storage area corresponding to the NAMDAT (SIDE, LED, COL, ADR) of the memory 70 via the amplifier circuit 19 and the A/D converter 20, wherein each variable is SIDE=0, LED=0, COL=1, and ADR=n (n is a value corresponding to the measurement position between 0 of the measurement starting position and the n of the measurement ending position).

When the green LED of the upper light source 11 is caused to emit light, a transistor of the green LED is turned ON (step S603), and a current setting value is outputted to the D/A converter 18G of the green LED (see FIG. 2) (step S604). After the light-reception output of the light-receiving element 13 is stabilized (YES in step S605), the light reflected on the top face of the conveyed bill 1 is received by the light-receiving element 13.

When collection of the reflected light data items on the top face of the bill 1 is ended, the reflected light being obtained by two-color emission at the upper light source 11 (YES in step S608), light is emitted in the order of the red LED and the green LED of the upper light source 12, and, as with the above-described process operation of collecting the reflected light data items on the top face of the bill 1, the reflected light being obtained from the two-color emission at the upper light source 11, the reflected light data items on the top face of the bill 1, which are obtained from red LED emission at the upper light source 12, are sequentially stored in the storage area corresponding to the NAMDAT (SIDE, LED, COL, ADR) of the memory 70, where each variable is SIDE=0, LED=1, COL=0, and ADR=n (n is a value corresponding to the measurement position between 0 of the measurement starting position and the n of the measurement ending position), whereby the data for one inserted bill 1 is stored in each of the storage areas.

Next, the reflected light data items on the top face of the bill 1, which are obtained from green LED emission at the upper light source 12, are sequentially stored in the storage area corresponding to the NAMDAT (SIDE, LED, COL, ADR) of the memory 70, where each variable is SIDE=0, LED=1, COL=1, and ADR=n (n is a value corresponding to the measurement position between 0 of the measurement starting position and the n of the measurement ending position), and the data for one inserted bill 1 is stored in each storage area.

When the reflected light data on the top face of the bill 1 at the measurement position on the inserted bill 1 is stored, the transistor of the green LED of the upper light source 12 is turned OFF, the current setting value of the D/A converter 18G of the green LED is set to 0 (step S606), and then the process of "collection of the reflected light data for each of the two colors (red, green) on the bottom face of the inserted bill 1, which is performed by the pearl light detecting sensor and non-pearl light detecting sensor" in the step S502 shown in FIG. 5 is performed.

Specifically, the two-color (red, green) LEDs of the lower light source 14 are sequentially caused to emit light, the data of the reflected light of each color at each measurement position on the bottom face of the inserted bill 1, which is received by the light-receiving element 16, and the data of the reflected light of each color at each measurement position on the bottom face of the inserted bill 1, which is received by the light-receiving element 15, are sequentially stored in the predetermined storage area, and the reflected light data items at each measurement position for one inserted bill 1 are collected.

In the process of collecting data items of the reflected light of each color by means of the pearl light detecting sensor and non-pearl light detecting sensor on the bottom face of the inserted bill 1, as shown in the flowchart of FIG. 7, the transistor of the red LED of the lower light source 14 is turned ON (steps S701, 702, 703), a current setting value is outputted to the D/A converter 18R of the red LED (see FIG. 2), and the red LED of the lower light source 14 is caused to emit light (step S704). After the light-reception output of the light-receiving element 16 is stabilized (YES in step S705), a light-reception output signal, which is outputted from the light-receiving element 16 in response to the reflected light on the bottom face of the bill 1, is amplified by the amplifier circuit 23, is converted into digital reflected light data by the A/D converter 24, and is stored in the storage area of NAMDAT (SIDE, PTX, COL, ADR) of the memory 70.

For the variable PTX of the NAMDAT (SIDE, PTX, COL, ADR), a value "0" indicating designation of the light-receiving element 16 and a value "1" indicating designation of the light-receiving element 15 are set, the data of the red reflected light on the bottom face of the inserted bill 1 which is detected by the pearl light detecting sensor is stored in the storage area of the NAMDAT (SIDE, PTX, COL, ADR) where SIDE=1, PTX=0, COL=0, and ADR=n (n is a value corresponding to the measurement position between 0 of the measurement starting position and the n of the measurement ending position).

When collection of the data items of the reflected light on the bottom face of the bill 1 is ended, the reflected light data being obtained from the red LED emission at the lower light source 14, the transistor of the red LED is turned OFF, the current setting value of the D/A converter 18R is set to 0 (step S706), the green LED of the lower light source 14 is caused to emit light, and the light-reception output signals, which are outputted from the light-receiving element 16 in response to the reflected light on the bottom face of the inserted bill 1 in the same manner as described above, are stored in the storage area corresponding to the NAMDAT (SIDE, PTX, COL, ADR) of the memory 70 via the amplifier circuit 23 and the A/D converter 24, wherein each variable is SIDE=1, PTX=0, COL=1, and ADR=n (n is a value corresponding to the measurement position between 0 of the measurement starting position and the n of the measurement ending position).

When the green LED of the lower light source 11 is caused to emit light, the transistor of the green LED is turned ON (step S703), and a current setting value is outputted to the D/A converter 18G (see FIG. 2) (step S704). After the light-reception output of the light-receiving element 16 is stabilized (YES in step S705), the light reflected on the bottom face of the bill 1 is received by the light-receiving element 16.

Once finishing the collection of the data items of the reflected light on the bottom face of the bill 1 which is obtained from the two-color emission at the lower light source 14 and from the light-receiving element 16, that is, the collection of data items of the reflected light of each of the two colors (red, green) on the bottom face of the inserted bill 1, the reflected light being detected by the pearl light detecting sensor (YES in step S708), data items of reflected light of each of the two colors (red, green) on the bottom face of the inserted bill 1 are collected, the reflected light being detected by the non-pearl light detecting sensor.

Specifically, as with the process operation of collecting the data items of the reflected light on the bottom face of the bill 1 which is obtained from the two-color emission at the lower light source 14 and from the light-receiving element 16, the two-color (red, green) LEDs of the lower light source 14 are sequentially caused to emit light, the light reflected on the bottom face of the bill 1 is received by the light-receiving element 15, and light-reception output signals which are outputted from the light-receiving element 15 are stored in the NAMDAT (SIDE, PTX, COL, ADR) of the memory 70 via the amplifier circuit 23 and A/D converter 24.

The data of the reflected light on the bottom face of the bill 1 which is obtained from the red LED emission at the lower light source 14 and from the light-receiving element 15 is stored in the storage area of the NAMDAT (SIDE, PTX, COL, ADR) where SIDE=1, PTX=1, COL=0, and ADR=n (n is a value corresponding to the measurement position between 0 of the measurement starting position and the n of the measurement ending position). The data of the reflected light on the bottom face of the bill 1 which is obtained from the green LED emission and from the light-receiving element 15 is stored in the storage area of the NAMDAT (SIDE, PTX, COL, ADR) where SIDE=1, PTX=1, COL=1, and ADR=n (n is a value corresponding to the measurement position between 0 of the measurement starting position and the n of the measurement ending position). The transistor of the green LED of the lower light source 14 is turned OFF, the current setting value of the D/A converter 18G is set to 0 (step S706), light of each color which transmits through the inserted bill 1 and obtained from the watermark sensor in the step S503 shown in FIG. 5 is received by the light-receiving element 15, and transmitted light data items are collected.

Specifically, as shown in the flowchart of FIG. 8, the two-color (red, green) LEDs of the upper light source 12 are sequentially caused to emit light, the light transmitting through the inserted bill 1 is received by the light-receiving element 15, and data items of the transmitted light of each color at each measurement position of the inserted bill 1 are collected for one inserted bill 1.

First, the transistor of the red LED is turned ON, a current value for the D/A converter 18R is set, and the red LED of the upper light source 12 is caused to emit light (steps S801, 802, 803). After a light-reception output of the light-receiving element 15 is stabilized (YES in step S804), the transmitted light of the conveyed bill 1 is detected by the light-receiving element 15, and light-reception output signals, to be outputted are stored in the storage area of the memory 70, which is associated with NAMDAT 2 (COL, ADR) of the memory 70, via the amplifier circuit 21 and A/D converter 22 (steps S805 and S806).

With regard to the variables of the NAMDAT 2 (COL, ADR), COL is managed as a value "0" indicating the red LED and a value "1" indicating the green LED, and ADR is managed as a value indicating information of the data collection position on the inserted bill 1. The data of the transmitted light on the inserted bill 1 which is obtained from the red LED emission at the upper light source 12 and from the light-receiving element 15 is stored in the storage area of the NAMDAT 2 (COL, ADR) where COL=0 and ADR=n (n is a value corresponding to the measurement position between 0 of the measurement starting position and the n of the measurement ending position).

When the collection of the data items of the transmitted light at the measurement position on the bill 1 is ended, the transmitted light obtained from the red LED emission of the upper light source 12 (NO in step S807), the green LED of the upper light source 12 is caused to emit light, the light transmitting through the bill 1 is received by the light-receiving element 15 as in the same manner described above, and the transmitted light data is stored in the storage are of the NAMDAT 2 (COL, ADR) where COL=1 and ADR=n (n is a value corresponding to the measurement position between 0 of the measurement starting position and the n of the measurement ending position). At the same time, the transistor of the green LED is turned OFF, the current setting value of the D/A converter 18G is set to 0 (step S805), and the process operation of collecting data items of the transmitted light of the conveyed bill 1 is ended, the transmitted light being obtained from two-color emission at the upper light source 12 and from the light-receiving element 15 (YES in the steps S806 and S807).

In this manner, by repeatedly performing, until the inserted bill 1 passes the optical detection section 10, collection of data items of the reflected light at the measurement position on each side of the inserted bill 1, the reflected light being obtained from the pearl light detecting sensor and non-pearl light detecting sensor, and collection of data items of the transmitted light of the inserted bill 1 which is obtained from the watermark sensor, the light-reception data items for the reflected light data and transmitted light data for one inserted bill 1 are collected.

As shown in the main flowchart of FIG. 4 described above, in the sheet recognizing device 100, when the magnetic data and the light-reception data of reflected light data or transmitted light data are detected by the magnetic sensor/transmitted light recognizing sensor and the like 89 or the optical detection section 10 at each measurement position of the inserted bill 1, and each light-reception data item for one inserted bill 1 is stored in the predetermined storage area of the memory 70 (YES in the step S406), the bill type and insertion direction determination section 40 of the microcomputer 95 determines the bill type and insertion direction (front and back, forward and reverse directions) of the inserted bill 1, on the basis of the magnetic data and the light-reception data which are detected by the magnetic sensor/transmitted light recognizing sensor and the like 89 (YES in the step S407).

When the bill type and insertion direction of the inserted bill 1 are determined by the bill type and insertion direction determination section 40, the watermark area data specifying section 46 refers to the watermark area data address reference table on the basis of the determined bill type and insertion direction of the inserted bill 1, then specifies the storage area of the memory 70 in which the light-reception data of the watermark area of the inserted bill 1 is stored, and then reads the reflected light data of the watermark area of the inserted bill 1 from the memory 70.

Then, the light-reception data correction section 45 corrects all of the reflected light data items of the bill 1 so that each of the light-reception output values for the red reflected light data and green reflected light data in the watermark area becomes a predetermined specified value, on the basis of the reflected light data of the watermark area of the inserted bill 1, which is read by the watermark area data specifying section 46.

Specifically, the light-reception output values of all of the reflected light data items collected from the inserted bill 1 are corrected so that the light-reception output value of each color (maximum light-reception output value) becomes 255 which is a correction standard value, at the measurement position in which, out of the reflected light data items of the watermark area on the inserted bill 1, which are detected by the pearl light detecting sensor of the optical detection section 10 and stored in the memory 70 in accordance with the bill type and insertion direction of the inserted bill 1, the sum of the light-reception output value of the red reflected light and the light-reception output value of the green reflected light becomes the maximum (maximum light-reception output) (the step S408).

It should be noted that the light-reception output value of the red reflected light data is referred to as "light-reception output value (red)", and the light-reception output value of the green reflected light data is referred to as "light-reception output value (green)".

The values at each measurement position on the inserted bill 1, which are subjected to color correction, are computed in the following Equation 1 and Equation 2.

When the red reflected light data is subjected to color correction, the values are computed by means of the following Equation 1.

> Corrected value (red) at each measurement position on the inserted bill 1=light-reception output value (red) of the reflected light data at each measurement position/maximum light-reception output value (red)×255.

When the green reflected light data is subjected to color correction, the values are computed by means of the following Equation 2.

> Corrected value (green) at each measurement position on the inserted bill 1=light-reception output value (green) of the reflected light data at each measurement position/maximum light-reception output value (green)×255.

It should be noted that the value "255" is obtained by setting a correction standard value to "255", and may be "100", thus it is not particularly limited.

Figure 9:
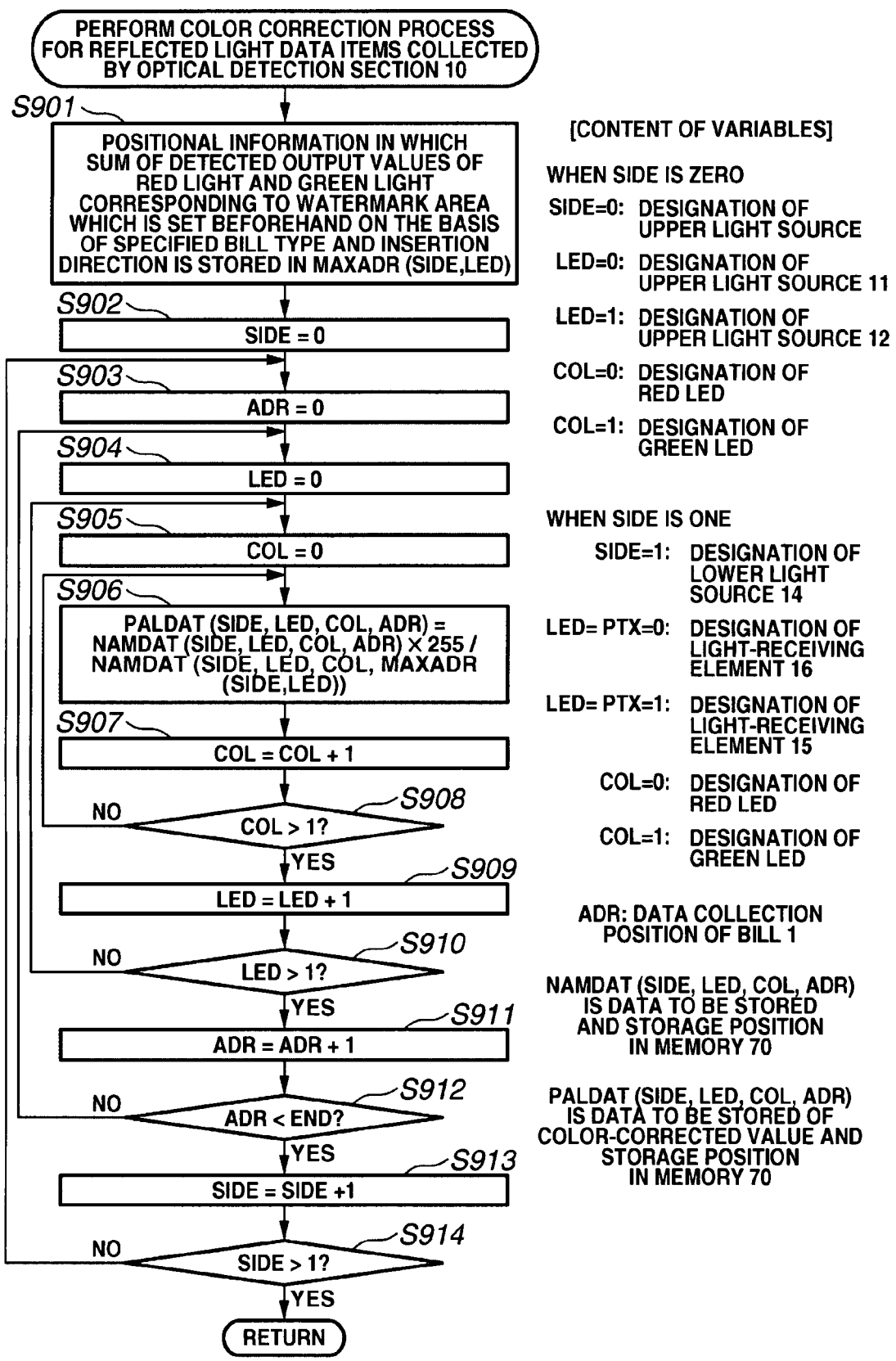
FIG. 9 is a flowchart showing a process operation of color correction of the collected reflected light data.

The detail of the process operation of this color correction is as shown in the flowchart of FIG. 9. First, on the basis of the reflected light data of the watermark area of the inserted bill 1, which is read from the NAMDAT (SIDE, LED, COL, ADR) of the memory 70 by the watermark area data specifying section 46, the light-reception data correction section 45 obtains measurement positions in which the sum of the light-reception output value of the red reflected light data and the light-reception output value of the green reflected light data at each measurement position within the watermark area becomes the maximum (maximum light-reception output), the light-reception output values being detected by the pearl light-detecting sensors. Then, as a pointer for reading the reflected light data of each color corresponding to the maximum light-reception output, the address of the memory 70 stored with the light-reception data of these measurement positions is stored in the storage area of a MAXADR (SIDE, LED) of the memory 70 (step S901).

The variable SIDE of the MAXADR (SIDE, LED) is set to a value "0" indicating designation of the upper light source or a value "1" indicating designation of the lower light source, the variable LED is set to "0" indicating designation of the upper light source 11 (when SIDE=0) or designation of the light-receiving element 16 (when SIDE=1), or a value "1" indicating designation of the upper light source 12 (when SIDE=0) or designation of the light-receiving element 15 (when SIDE=1).

Specifically, the sum of the light-reception output value (red) of the red reflected light data and the light-reception output value (green) of the green reflected light data is sequentially detected, the red and green reflected light being detected by the pearl light detecting sensor constituted by the upper light source 11 and the light-receiving element 13 at each measurement position inside the watermark area of the inserted bill 1. Then, the light-reception output value of the reflected light data of each color at which the sum of the light-reception output value (red) of the red reflected light data and the light-reception output value (green) of the green reflected light data becomes the maximum (maximum light-reception output), and the address for the reflected light data of each color stored in the memory 70 are specified, and the specified address is stored in the MAXADR (SIDE, LED) where SIDE=0 and LED=0, as positional information of the light-reception data corresponding to the maximum light-reception output.

Further, position information at which the sum of the light-reception output value (red) of the red reflected light data and the light-reception output value (green) of the green reflected light data becomes the maximum is computed using the same method described above, the red and green reflected light being detected by the non-pearl light detecting sensor constituted by the upper light source 12 and the light-receiving element 13, and the address of the reflected light data of each color is stored in the MAXADR (SIDE, LED) where SIDE=0 and LED=1.

Furthermore, an address at which the sum of the light-reception output value (red) of the red reflected light data and the light-reception output value (green) of the green reflected light data becomes the maximum (maximum light-reception output) is specified using the same method described above, the red and green reflected light being detected respectively by the pearl light detecting sensor constituted by the lower light source 14 and the light-receiving element 16 and the non-pearl light detecting sensor constituted by the lower light source 14 and the light-receiving element 15, the address of the reflected light data of each color of the maximum light-reception output is stored in the MAXADR (SIDE, LED) where SIDE=1 and LED=0, the reflected light being detected by the pearl light detecting sensor constituted by the lower light source 14 and the light-receiving element 16, and the address of the reflected light data of each color of the maximum light-reception output is stored in the MAXADR (SIDE, LED) where SIDE=1 and LED=1, the reflected light being detected by the non-pearl light detecting sensor constituted by the lower light source 14 and the light-receiving element 15.

When the positional information at which the sum of the light-reception output value (red) of the red reflected light data and the light-reception output value (green) of the green reflected light data becomes maximum is stored in the MAXADR (SIDE, LED) of the memory 70, the red and the green reflected light being detected by the pearl light detecting sensor of the watermark area of the inserted bill 1, color correction of the light-reception output value of each of the red and the green reflected light data items which are collected at the measurement position on each side of the inserted bill 1 is computed with respect to the red reflected light data by using the above Equation 1, and is also computed with respect to the green reflected light data by using the above Equation 2. Results of the computation are stored in the storage area associated with PALDAT of the memory 70.

Specifically, the computation is performed using the following Equation 3.

> PALDAT(SIDE,LED,COL,ADR)=NAMDAT(SIDE, LED,COL,ADR)×255/NAMDAT(SIDE,LED, COL,MAXADR(SIDE,LED)).

In the above Equation 3, a corrected value of the light-reception output value (red) of the data of the red reflected light at the measurement starting position on the top face of the inserted bill 1 is computed by means of SIDE=0, LED=0, COL=0, ADR=0, and MAXADR (SIDE, LED), the red reflected light being detected by the pearl light detecting sensor which is constituted from the upper light source 11 and the light-receiving element 13. A corrected value of the light-reception output value (green) of the green reflected light data is computed by means of SIDE=0, LED=0, COL=1, ADR=0, and MAXADR (SIDE, LED). The corrected values are then stored in the storage areas PALDAT (SIDE, LED, COL, ADR) (YES in step S902 through step S908).

Moreover, in the above Equation 3, a corrected value of the light-reception output value (red) of the red reflected light at the measurement starting position on the top face of the inserted bill 1 is computed by means of SIDE=0, LED=1, COL=0, ADR=0, and MAXADR (SIDE, LED), the red reflected light being detected by the non-pearl light detecting sensor which is constituted from the upper light source 12 and the light-receiving element 13. A corrected value of the light-reception output value (green) of the green reflected light data is computed by means of SIDE=0, LED=1, COL=1, ADR=0, and MAXADR (SIDE, LED). The corrected values are then stored in the storage areas PALDAT (SIDE, LED, COL, ADR) (step S909, NO in step S910). By repeating the process, which is similar to the process between the step S905 and the step S910, until the measurement starting end position (ADR=0, 1, 2, ..., n) of the top face of the inserted bill 1 is reached, the corrected values of the light-reception output values of the data items for the red and green reflected light detected by the pearl light detecting sensor of the top face of the inserted bill 1 are computed, and the computed corrected values are stored in the predetermined storage areas PALDAT (SIDE, LED, COL, ADR) (YES in step S904 through step S912).

Once computing the corrected values of the light-reception output values of the data items for the red and green reflected light detected by the pearl light detecting sensor of the top face of the inserted bill 1, and storing the computed corrected values in the predetermines storage areas PALDAT (SIDE, LED, COL, ADR), the color correction process similar to the one described above is performed for the light-reception output values of the data items for the red and green reflected light detected by the pearl light detecting sensor of the bottom face of the inserted bill 1.

Specifically, in the above Equation 3, a corrected value of the light-reception output value (red) of the data of the red reflected light at the measurement starting position on the bottom face of the inserted bill 1 is computed by means of SIDE=1, LED=PTX=0, COL=0, ADR=0, and MAXADR (SIDE, LED), the red reflected light being detected by the pearl light detecting sensor which is constituted from the lower light source 14 and the light-receiving element 16. A corrected value of the light-reception output value (green) of the green reflected light data is computed by means of SIDE=1, LED=PTX=0, COL=1, ADR=0, and MAXADR (SIDE, LED). The corrected values are then stored in the storage areas PALDAT (SIDE, LED, COL, ADR) (step S913, NO in step S914, step S903 through step S908).

Moreover, in the above Equation 3, a corrected value of the light-reception output value (red) of the data of the red reflected light at the measurement starting position on the bottom face of the inserted bill 1 is computed by means of SIDE=1, LED=PTX=1, COL=0, ADR=0, and MAXADR (SIDE, LED), the red reflected light being detected by the non-pearl light detecting sensor which is constituted from the lower light source 14 and the light-receiving element 15. A corrected value of the light-reception output value (green) of the green reflected light data is computed by means of SIDE=1, LED=PTX=1, COL=1, ADR=0, and MAXADR (SIDE, LED). The corrected values are then stored in the storage areas PALDAT (SIDE, LED, COL, ADR) (step S909, NO in step S910, step S905 through step S910). By repeating the process, which is similar to the process between the step S905 and the step S910, until the measurement starting end position (ADR=0, 1, 2, ..., n) of the bottom face of the inserted bill 1 is reached, the corrected values of the light-reception output values of the data items for the red and green reflected light detected by the pearl light detecting sensor of the bottom face of the inserted bill 1 are computed, and the computed corrected values are stored in the predetermined storage areas PALDAT (SIDE, LED, COL, ADR) (the step S904 through step S912, YES in the step S912).

In this manner, once finishing the color correction process of the light-reception data correction section 45 for the reflected light data of each color on each side of the inserted bill 1, the reflected light data being collected by the optical detection section 10, the process of determining whether the inserted bill 1 is a counterfeit ticket or not is performed on the basis of the reflected light data of each color which is subjected to the color correction processing (referred to as "color-corrected data item" hereinafter) (see step S409 in FIG. 4).

The pearl data determination section 50 performs this determination processing for determining whether the inserted bill 1 is a counterfeit ticket or not, on the basis of the color tone and pearl ink component of the ink at the position of measurement on each side of the inserted bill 1, which are obtained from the color-corrected data, and on the basis of the judging standard therefore.

Figure 10:
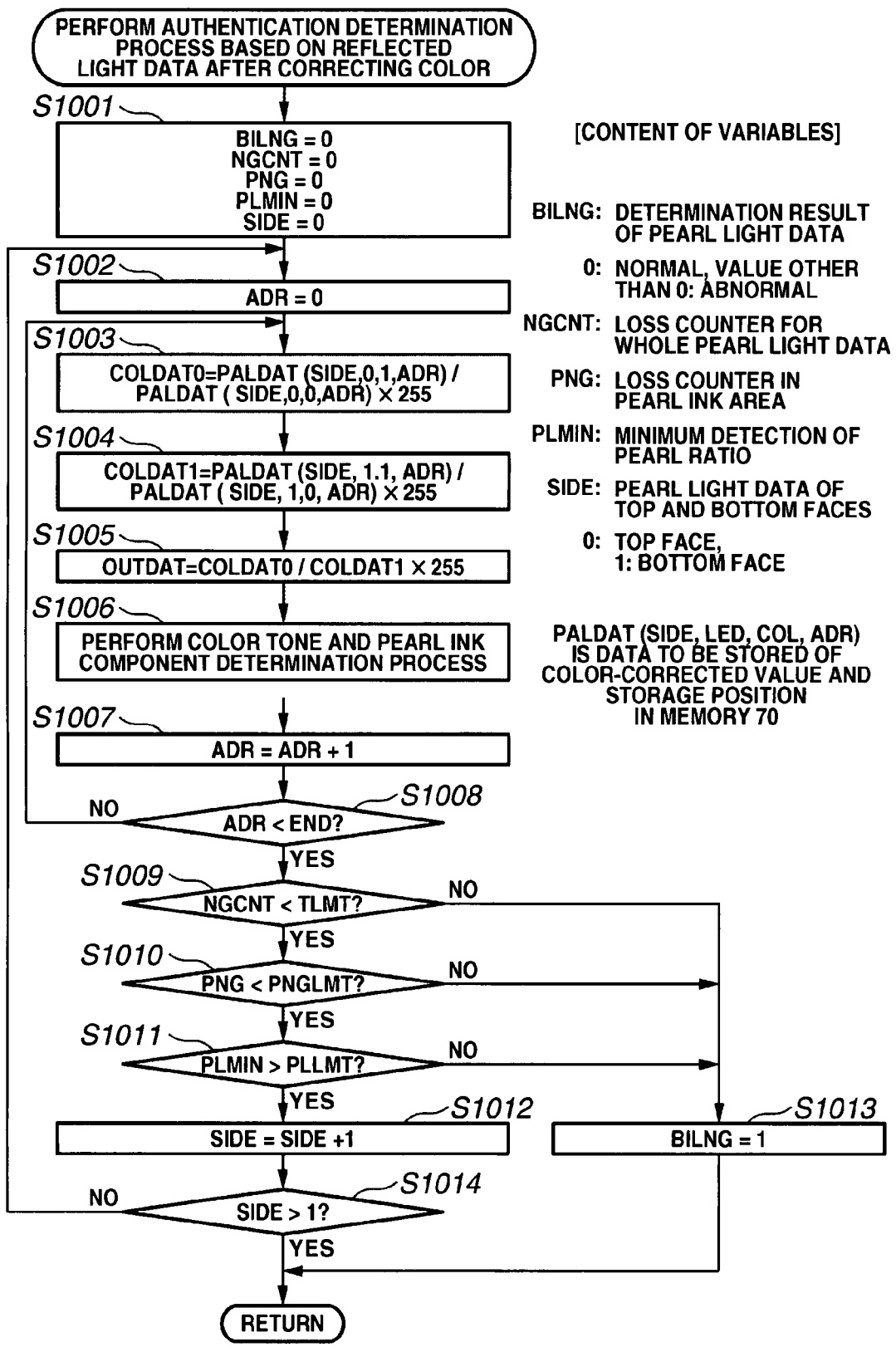
FIG. 10 is a flowchart showing a process operation for authentication determination on the basis of the reflected light data after color correction is performed.

Specifically, as shown in the flowchart of FIG. 10, after initializing the storage area which stores each value of an authentication recognizing flag BILNG, a counter NGCNT, PNG, the minimum value PLMIN of the pearl ink component, SIDE designating the top and bottom faces of the inserted bill 1, and the like (step S1001), the ratio (red-green ratio (oblique light beam)) COLDAT 0 between red corrected data and green corrected data of the reflected light data collected by the pearl light detecting sensor at the measurement position on each side of the inserted bill 1, the ratio (red-green ratio (vertical light beam)) COLDAT 1 between red corrected data and green corrected data of the reflected light data collected by the non-pearl light detecting sensor at the measurement position on each side of the inserted bill 1, and the ratio (ratio between red-green ratios) OUTDAT between the red-green ratio (oblique light beam) and the red-green ratio (vertical light beam) are computed (step S1002, step S1003, step S1004, and step S1005). A result of comparison between each of the computed values and an allowable value (upper limit value, lower limit value) acquired from the authentic bill beforehand is computed in "a process of determining the color tone and pearl ink component", and the process of determining whether the bill 1 is a counterfeit ticket or not is performed on the basis of the result of the comparison.

It should be noted that the detail of the "process of determining the color tone and pearl ink component" is described hereinafter.

Information containing a color tone of the ink printed on the inserted bill 1 can be obtained from the computed red-green ratio (vertical light beam) COLDAT 1, and information on the pearl ink component printed on the inserted bill 1 can be obtained from the ratio between red-green ratios OUTDAT. Therefore, on the basis of the color tone (red-green ratio (vertical light beam) COLDAT 1) value and pearl ink component (ratio between red-green ratios OUTDAT) value at the measurement position on each side on the authentic bill, which are collected from a number of authentic values in advance, a lower limit value CLOWLMT (KIN, INS, ADR) and an upper limit value CHILMT (KIN, INS, ADR) of the ratio between red-green ratios (vertical light beam) COLDAT 1 value of the authentic bill, and a lower limit value LOWLMT (KIN, INS, ADR) and an upper limit value HILMT (KIN, INS, ADR) of the ratio between red-green ratios OUTDAT value are set in consideration of variation of each value, and the number of times that red-green ratio (vertical light beam) COLDAT 1 value (color tone) and the ratio between red-green ratios OUTDAT value at each measurement position on the inserted bill 1 exceed the lower limit value or upper limit value of the red-green ratio (vertical light beam) COL-DAT 1 value (color tone) and the ratio between red-green ratios OUTDAT value of the authentic bill is counted, whereby recognition of the authentication can be performed on the basis of the color tone and pearl ink component of the ink formed on the inserted bill 1 and on the basis of the judging standard.

It should be noted that the ratio between red-green ratios OUTDAT value indicates a large value (in the vicinity of 255, for example) in an area in which the pearl ink is not printed (a colorless area, a colored printed area, and the like), and indicates a small value in an area in which the pearl ink is printed.

The red-green ratio (oblique light beam) COLDAT 0 is computed in the following Equation 4.

$$COLDAT\ 0 = PALDAT(SIDE,0,1,ADR)/PALDAT(SIDE,0,0,ADR) \times 255.$$

In the above Equation 4, the red-green ratio (oblique light beam) between the red corrected data and green corrected data of the reflected light data at each measurement position on the top face of the inserted bill 1, the reflected light being originated from light emission of the upper light source 11 and light reception of the light-receiving element 13 (pearl light detecting sensor), is indicated by SIDE=0 and ADR=n (n is a value corresponding to the measurement position between 0 of the measurement starting position and the n of the measurement ending position), and the red-green ratio (oblique light beam) between the red corrected data and green corrected data of the reflected light data at each measurement position on the bottom face of the inserted bill 1, the reflected light being originated from light emission of the lower light source 14 and light reception of the light-receiving element 16 (pearl light detecting sensor), is indicated by SIDE=1 and ADR=n (n is a value corresponding to the measurement position between 0 of the measurement starting position and the n of the measurement ending position).

Further, the red-green ratio (vertical light beam) COLDAT 1 is computed in the following Equation 5.

$$COLDAT\ 1 = PALDAT(SIDE,1,1,ADR)/PALDAT(SIDE,1,0,ADR) \times 255.$$

In the above Equation 5, the red-green ratio (vertical light beam) between the red corrected data and green corrected data of the reflected light data at each measurement position on the top face of the inserted bill 1, the reflected light being originated from light emission of the upper light source 12 and light reception of the light-receiving element 13 (non-pearl light detecting sensor), is indicated by SIDE=0 and ADR=n (n is a value corresponding to the measurement position between 0 of the measurement starting position and the n of the measurement ending position), and the red-green ratio (vertical light beam) between the red corrected data and green corrected data of the reflected light data at each measurement position on the bottom face of the inserted bill 1, the reflected light being originated from light emission of the lower light source 14 and light reception of the light-receiving element 15 (non-pearl light detecting sensor), is indicated by SIDE=1 and ADR=n (n is a value corresponding to the measurement position between 0 of the measurement starting position and the n of the measurement ending position).

Further, the ratio between red-green ratios OUTDAT between the red-green ratio (oblique light beam) COLDAT 0 and the red-green ratio (vertical light beam) COLDAT 1 is computed in the following Equation 6.

$$OUTDAT = COLDAT0/COLDAT1 \times 255.$$

When the red-green ratio (vertical light beam) COLDAT 1 and the ratio between red-green ratios OUTDAT of the measurement position on each side of the inserted bill 1 are computed, the result of comparison between each of the computed values and the allowable value (upper limit value, lower limit value) acquired from the authentic bill beforehand is computed in the "process of determining the color tone and pearl ink component" (step S1006).

Figure 11:
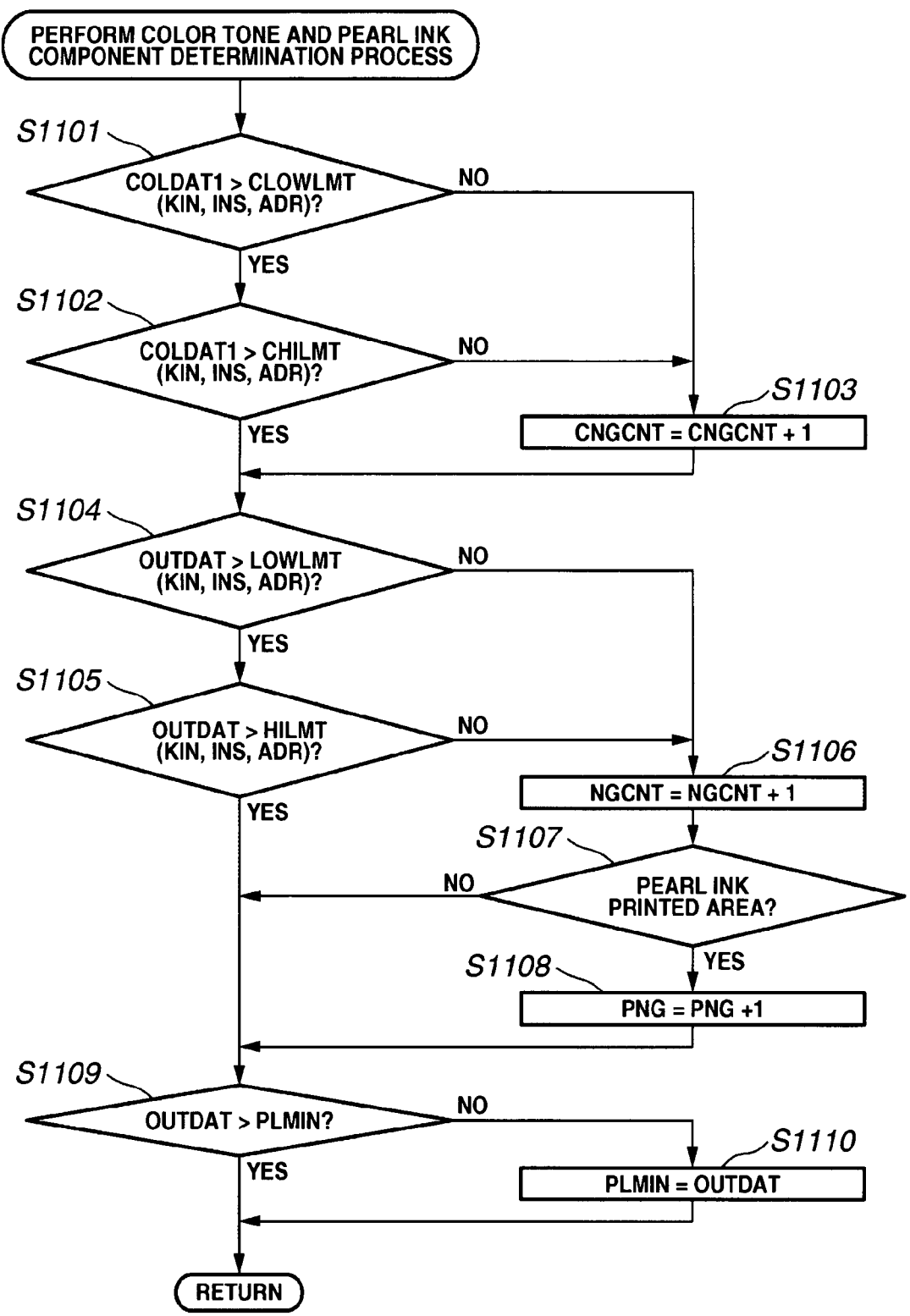
FIG. 11 is a flowchart showing a process operation for determining a color tone and pearl ink component.

In this "process of determining the color tone and pearl ink component", as shown in the flowchart of FIG. 11, when the red-green ratio (vertical light beam) COLDAT 1 value between the red corrected data of the red reflected light data and the green corrected data of the green reflected data of the inserted bill 1, which are collected by the non-pearl light detecting sensor, falls below the lower limit value CLOW-LMT (KIN, INS, ADR) or exceeds upper limit value CHILMT (KIN, INS, ADR) of the authentication judging standard (NO in step S1101, NO in step S1102), that is, when the color tone at the measurement position on each side of the inserted bill 1 is outside the allowable range of color tones collected from the authentic bill, the counter CNGCNT is counted up (step S1103). When the ratio between red-green ratios OUTDAT between the red-green ratio (oblique light beam) COLDAT 0 and the red-green ratio (vertical light beam) COLDAT 1 at the measurement position on each side of the inserted bill 1 falls below the lower limit value LOW-LMT (KIN, INS, ADR) or exceeds upper limit value HILMT (KIN, INS, ADR) of the authentication judging standard (NO in step S1104, NO in step S1105), that is, when the indicating the pearl ink component of the measurement position on each side of the inserted bill 1 exceeds the allowable range of values indicating the pearl ink component, which are collected from the authentic bill, the counter NGCNT is counted up (step S1106). Moreover, if the measurement position is within an area in which the pearl ink of the inserted bill 1 is printed (YES in step S1107), the minimum value PLMIN of the ratio between red-green ratios OUTDAT of the inserted bill 1 is detected (step S1109, step S1110) after the counter PNG is counted up (step S1108), and each of the counter values CNGCNT, NGCNT, and PNG, and the minimum value PLMIN of the ratio between red-green ratios OUTDAT for one inserted bill 1 are detected.

Whether or not each measurement position is inside the area in which the pearl ink of the inserted bill 1 is printed can be discriminated by referring to the pearl ink printed section data address reference table stored in the memory 70.

As shown in the flowchart of FIG. 10, when each of the counter values NGCNT and PNG and the minimum value PLMIN of the ratio between red-green ratios OUTDAT for one inserted bill 1 are detected (YES in the step S1008), the authentication of the inserted bill 1 is determined on the basis of these values.

Specifically, the counter value NGCNT at which the pearl ink component value of the inserted bill 1 is outside of the allowable range is discriminated. In other words, whether or not the number of missing pearl light data items in the entire inserted bill 1 exceeds a predetermined authentication judging standard value TLMT is discriminated (step S1009). When it is exceeded (NO in the step S1009), the authentication recognizing flag BILNG is set to "1" (step S1013), thereafter the inserted bill 1 is determined as a counterfeit ticket, and then the process is ended.

Further, if the counter value NGCNT is within the range of the predetermined authentication judging standard value TLMT (YES in the step S1009), the counter value PNG at which the pearl ink component value in the area in which the pearl ink of the inserted bill 1 is printed is outside of the allowable range is discriminated. In other words, whether or not the number of missing pearl ink areas in the inserted bill 1 exceeds a predetermined authentication judging standard value PNGLMT is discriminated (step S1010). When it is exceeded (NO in the step S1010), the authentication recognizing flag BILNG is set to "1" (step S1013), thereafter the inserted bill 1 is determined as a counterfeit ticket, and then the process is ended.

Further, if the counter value PNG is within the range of the predetermined authentication judging standard value PNGLMT (YES in the step S1010), it is discriminated whether the minimum value PLMIN of the ratio between the red-green ratios OUTDAT of the inserted bill 1 is larger than the predetermined authentication judging standard value PLLMT or not (step S1011). If it is smaller than the predetermined authentication judging standard value PLLMT (NO in the step S1011), the authentication recognizing flag BILNG is set to "1" (step S1013), thereafter the inserted bill 1 is determined as a counterfeit ticket, and then the process is ended.

As described above, in the sheet recognizing device and method of the present invention, color correction is performed on all of the reflected light data items of the inserted bill 1, which are collected by the optical detection section 10, in order to constrain variation of recognition and determination due to variation of the amount of emitted light or the light-reception sensitivity, which is caused by time degradation of the light sources and light-receiving elements of the optical detection section 10, and the characteristics of the pearl ink are recognized precisely by comparing a standard value with the computed values of the color tone and pearl ink components of the ink printed on the inserted bill 1, at each measurement position, the color tone and pearl ink component being obtained based on the color correction data. Therefore, it is possible to discriminate, with a high degree of accuracy, whether the pearl ink printed on the inserted bill 1 is a unique pearl ink printed on an authentic bill or other inks.

When it is determined that the inserted bill 1 is not a counterfeit ticket, on the basis of the reflected light data after color correction (color-corrected data) (No in the step S410), the process of determining whether the inserted bill 1 is an authentic bill or not is performed on the basis of the reflected light data and transmitted light data of the watermark area of the inserted bill 1 (step S411).

In the "authentication determination processing of the watermark area" in the step S411, specifically, whether a watermark pattern corresponding to a watermark design is detected or not on the basis of the transmitted light data of the watermark area of the inserted bill 1, and whether the watermark pattern is detected or not on the basis of the reflected light data of the watermark area.

For example, when light is projected to an authentic bill in which a watermark area is formed and to a counterfeit ticket in which a watermark is not formed, to detect a light-reception output of each transmitted light beam, a watermark pattern is detected for the authentic bill, while a watermark pattern is not detected for the counterfeit ticket. Thus, recognition of the authentic bill and counterfeit ticket can be performed easily on the basis of whether a watermark is detected or not.

However, in the case of a counterfeit ticket in which a watermark area is copied or is marked with a doodle, a watermark pattern is detected. Therefore, it is difficult to recognize the authentic bill and the counterfeit ticket on the basis of whether a watermark pattern is detected from the transmitted light.

On the other hand, when light is projected to an authentic bill in which a watermark area is formed and to a counterfeit ticket in which a watermark area is not formed, to detect a light-reception output of each reflected light beam, a watermark pattern cannot be detected in the authentic bill and the counterfeit ticket. However, in the case of a counterfeit ticket in which a watermark area is copied or is marked with a doodle, a watermark pattern is detected. Therefore, the authentic bill and the counterfeit ticket can be recognized by discriminating whether a watermark pattern from the transmitted light and reflected light is detected.

Figure 12:
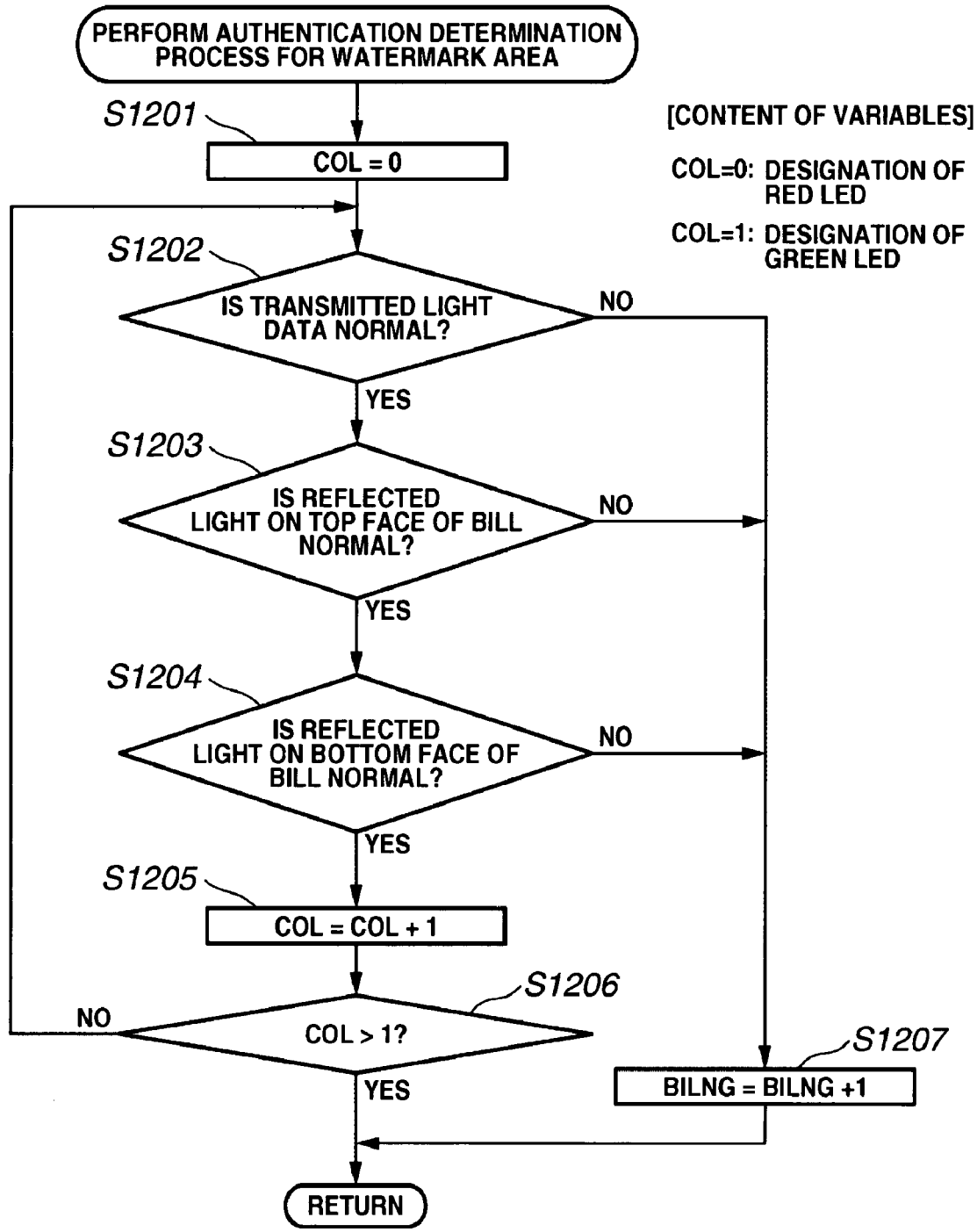
FIG. 12 is a flowchart showing a process operation for determining the authentication of a watermark area of the inserted bill 1.

According to these facts, as shown in the flowchart of FIG. 12, when a watermark pattern is not detected on the basis of red transmitted light data of a watermark on the inserted bill 1, which is detected from light emission of the red LED of the upper light source 12 configuring the watermark sensor, and from light reception of the light-receiving element 15 (step S1201, N in step S1202), the authentication recognizing flag BILNG is counted up (step S1207), thereafter the inserted bill 1 is determined as a counterfeit ticket, and then the operation of "authentication determination processing for the watermark area" in the step S411 is ended.

In the step S1202, when a watermark pattern is detected (YES in the step S1202), and when a watermark pattern is detected on the basis of the red reflected light data of the watermark area on the top face of the inserted bill 1, the red reflected light being detected by light emission of the red LED of the upper light source 12 and light reception of the light-receiving element 13 (NO in step S1203), the authentication recognizing flag BILNG is counted up (step S1207), thereafter the inserted bill 1 is determined as a counterfeit ticket, and then the process is ended.

In the step S1203, when a watermark pattern is not detected (YES in the step S1203), and when a watermark pattern is detected on the basis of the red reflected light data of the watermark area on the bottom face of the inserted bill 1, the red reflected light being detected by light emission of the red LED of the lower light source 14 and light reception of the light-receiving element 15 (NO in step S1204), the authentication recognizing flag BILNG is counted up (step S1207), thereafter the inserted bill 1 is determined as a counterfeit ticket, and then the process is ended.

In the step S1204, when a watermark pattern is not detected (YES in the step S1204), the determination operations from the step S1202 through the step S1204 described above are repeated on the basis of the green transmitted light or reflected light data of the watermark on the top face or bottom face of the inserted bill 1, the green transmitted light or reflected light being detected by light emission of the green light LED of the upper light source 12 or lower light source 14 and light reception of the light-receiving element 13 or light-receiving element 15, and thereafter the authentication determination processing for the watermark area is ended (YES in step S1206).

In this manner, by performing the process in which the determination processes based on the transmitted light data and reflected light data of the watermark area of the inserted bill 1 are combined, the authentication of the inserted bill 1 can be determined. By collecting the transmitted light data items and reflected light data items by emitting light of two wavelengths, the accuracy of recognizing the authentication of the inserted bill 1 is further improved.

Figure 13:
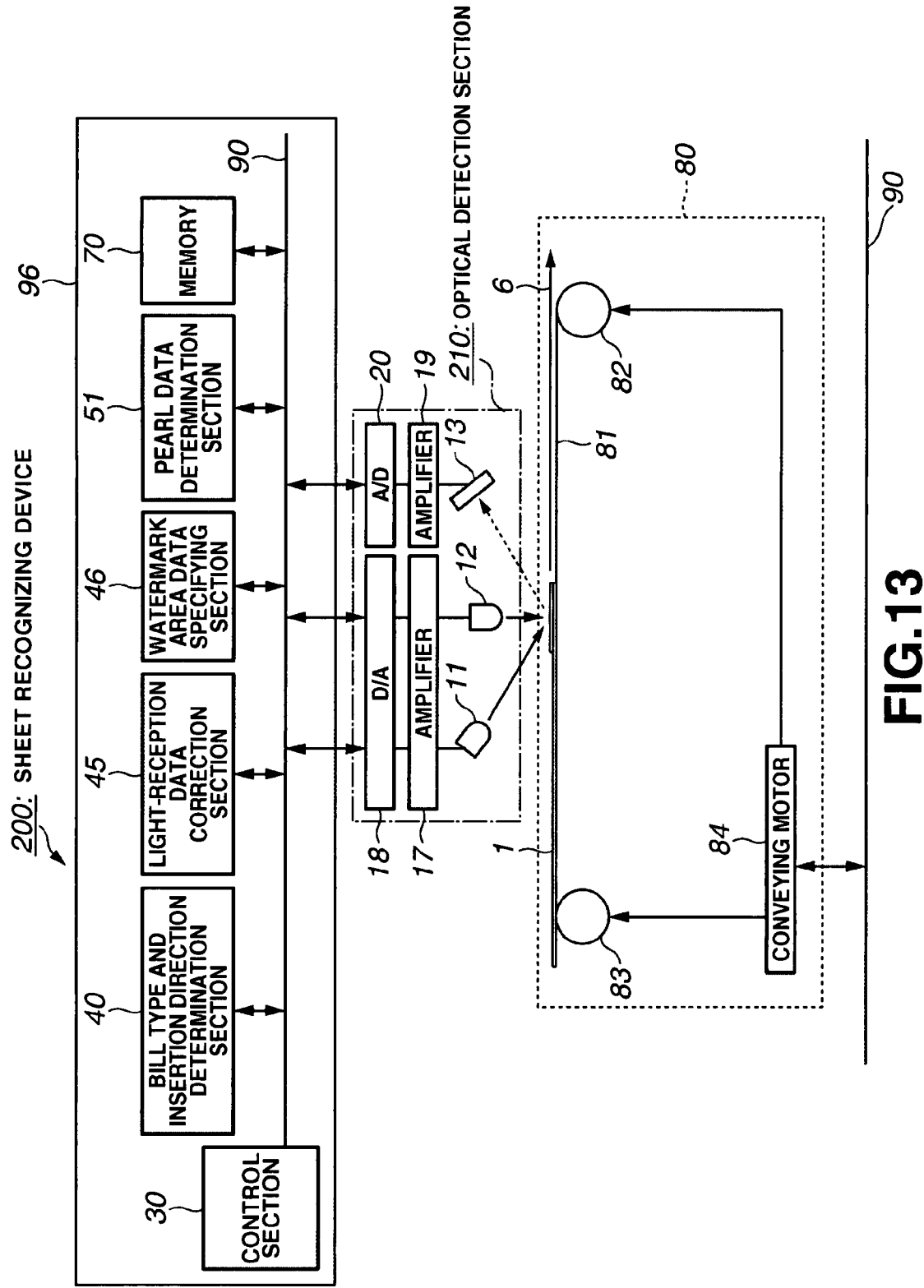
FIG. 13 is a block diagram showing a configuration example of a sheet recognizing device 200 according to the present invention.
Figure 14:
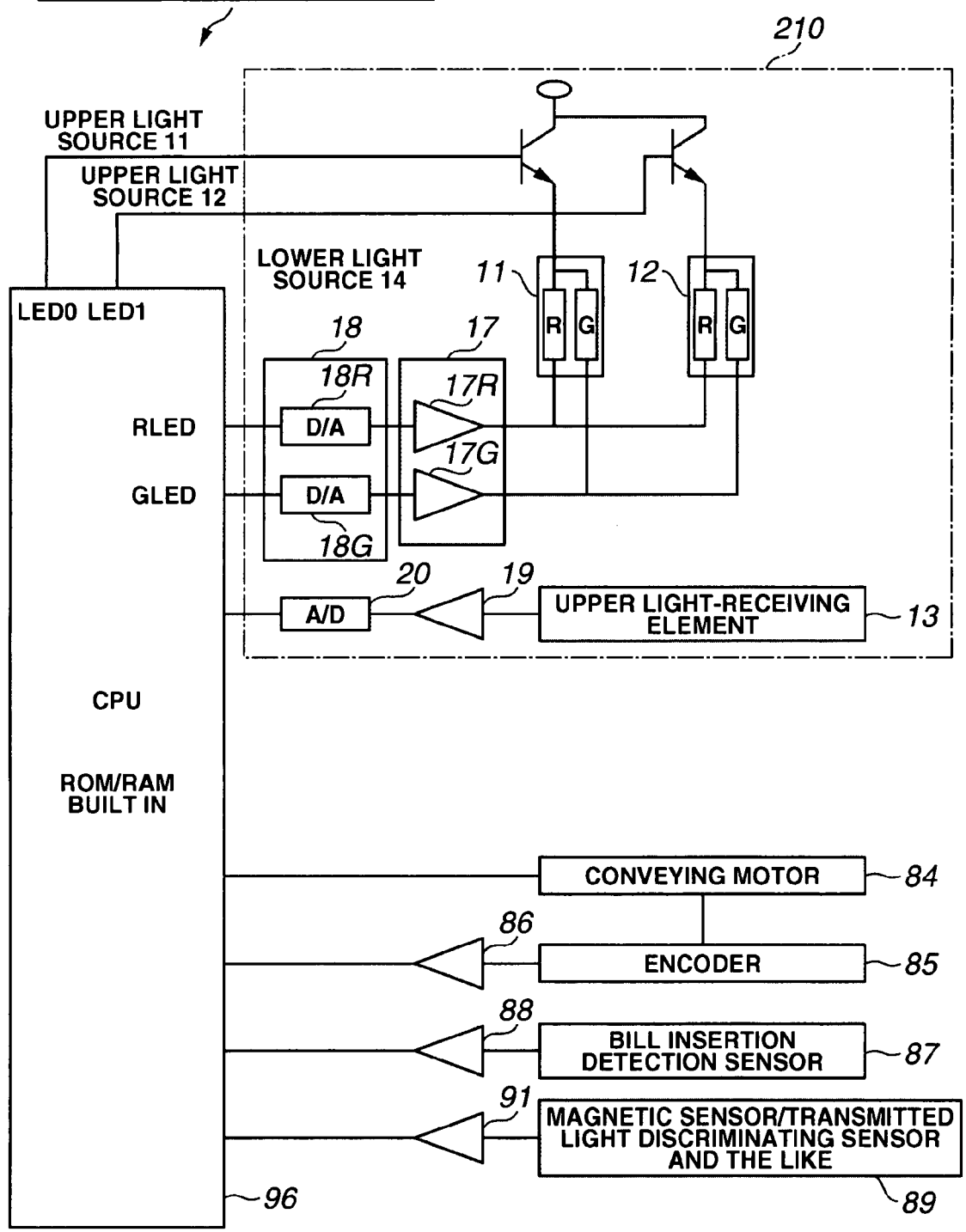
FIG. 14 is a circuit block diagram showing an example of a circuit configuration of the sheet recognizing device 200.

FIG. 13 is a block diagram showing a configuration example of a sheet recognizing device 200 according to the present invention, which is different from the sheet recognizing device 100 described above. FIG. 14 is a circuit block diagram showing an example of a circuit configuration of the sheet recognizing device 200.

The configuration example of the sheet recognizing device 200 is such that, by inserting a bill, only one side of which is printed with a pearl ink, in a specified insertion direction for the front and back of the bill, the authentication recognition is performed precisely on the pearl ink printed on the bill.

As shown in FIG. 13 and FIG. 14, the sheet recognizing device 200 comprises an optical detection section 210 in which are disposed upper light sources 11 (first light source) and 12 (second light source) for projecting two colors (red, green) from an oblique direction and a vertical direction to the top face of the inserted bill 1, and a light-receiving element 13 (first light-receiving element) for receiving light reflected on the top face of the inserted bill 1.

It should be noted that, for the convenience of explanation, the configurations and operating parts of the sheet recognizing device 200 shown in FIGS. 13 and 14, which are same as those of the sheet recognizing device 100 shown in FIG. 1 and FIG. 2, applied with the same reference numerals, and explanations thereof are omitted so as to refer to the above descriptions.

As shown in FIG. 13 and FIG. 14, in the configuration of the sheet recognizing device 200 comprising the optical detection section 210 as well, the authentication of the inserted bill 1 is discriminated on the basis of a color tone depending on or independent of a pearl ink on the top face of the inserted bill 1, or on the basis of the pearl ink component or color tone in an area in which the pearl ink is printed, whereby the accuracy of recognizing the authentication of the inserted bill 1 can be further improved.

Figure 15:
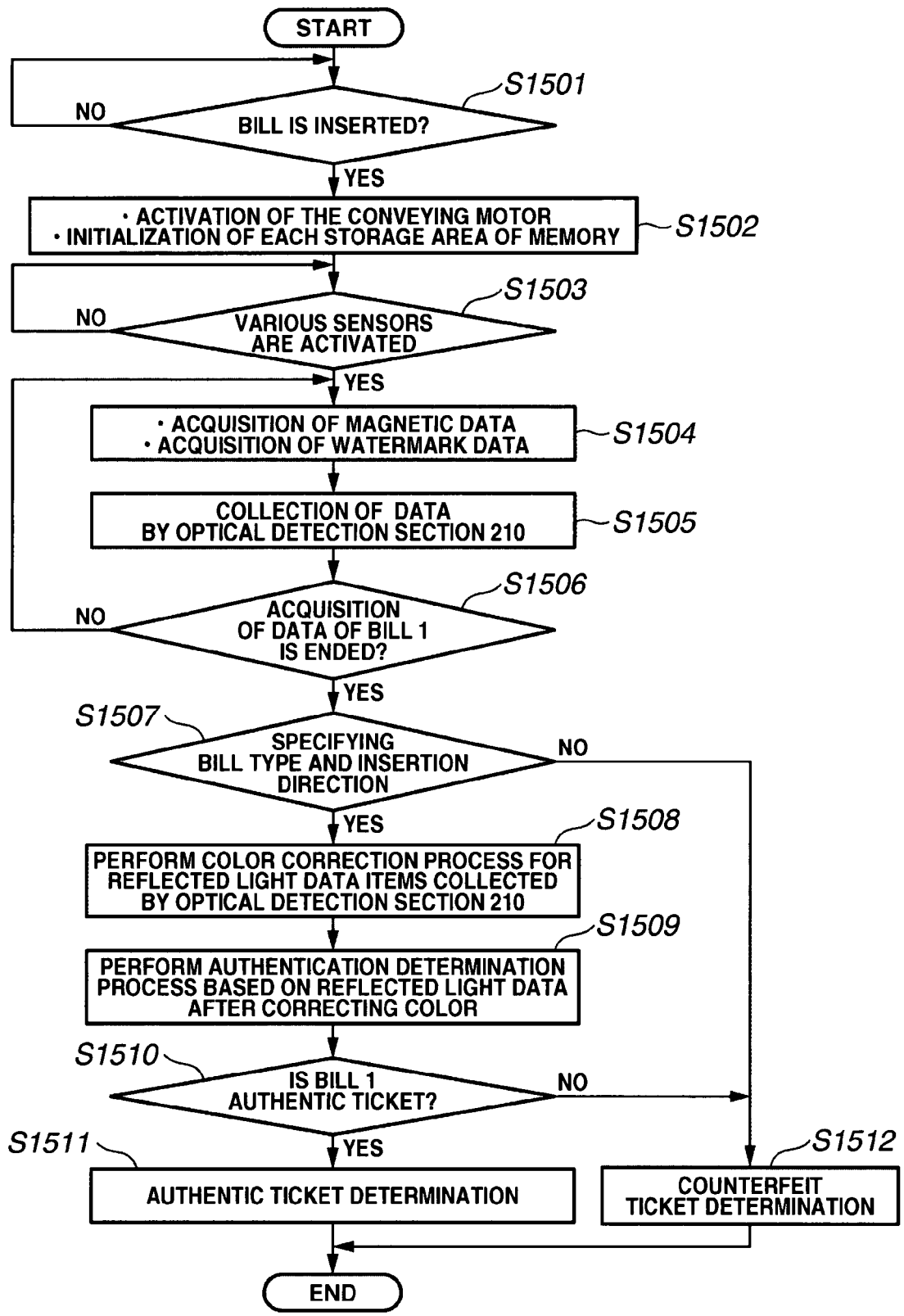
FIG. 15 is a schematic flowchart showing a process operation in which the sheet recognizing device 200 recognizes the authentication of the inserted bill 1.

Specifically, as shown in the schematic flowchart of a process operation of authentic recognition of the sheet recognizing device 200, which is shown in FIG. 15, when the bill 1 is inserted at a predetermined insertion direction (front and back), the bill insertion detection sensor 87 detects that the bill 1 is inserted (YES in step S1501), the conveying motor 84 is activated to convey the inserted bill 1, and a predetermined storage area of the memory 70 is initialized (step S1502), and thereafter each sensor of the magnetic sensor/transmitted light recognizing sensor and the like 89, optical detection section 10, and the like are activated (YES in step S1503).

Magnetic data or data in the watermark area at each measurement position on the top face of the inserted bill 1 is detected by the magnetic sensor/transmitted light recognizing sensor and the like 89, and data items of the reflected light of two colors (red, green) are detected by respective sensor of the optical detection sensor 10 and the like, and data on the inserted bill for one sheet are stored sequentially in the predetermined storage areas of the memory 70 (step S1504, step S1505).

It should be noted that the process operation of "data collection performed by the optical detection section 210" in the step S1505 is same as the process operation of "collection of the reflected light data on the top face of the inserted bill 1, which is performed by the pearl light detecting sensor and non-pearl light detected sensor" as shown in FIG. 6, thus the detailed description thereof is omitted.

After data items for one inserted bill 1 are collected by each sensor (YES in step S1506), color correction is performed on the basis of specified reflected light data of the watermark area on the top face of the inserted bill 1 corresponding to the bill type and insertion direction of the inserted bill 1, which are determined by the bill type and insertion direction determination section 40 (step S1508), the process of determining the authentication of the inserted bill 1 is performed on the basis each of the color-corrected data items which are subjected to color correction (step S1509), and the bill 1 is determined as an authentic bill (YES in step S1510) or counterfeit ticket (NO in the step S1510) on the basis of a result of the determination.

It should be noted that "the color correction process for the reflected light data items collected by the optical detection section 210" in the step S1508 is same as the process operation when SIDE=0 in "the color correction process for the reflected light data items collected by the optical detection section 10" shown in FIG. 9, and "the authentication determination process based on the reflected light data after color correction" in the step S1509 is same as the process operation when SIDE=0 in "the authentication determination process based on the reflected light data after color correction" shown in FIGS. 10 and 11, and as the process operation of "the color tone and pearl ink component determination process". Therefore, the detailed explanation for these processes is omitted.

As described above, in the sheet recognizing device 200, although the authentication determination process based on the transmitted light of the watermark area of the inserted bill 1 is not performed, color tone recognition, pearl ink component recognition, and pearl ink area recognition are performed based on the reflected light of two colors on the top face of the inserted bill 1, thus the accuracy of recognizing the inserted bill 1 is further improved.

Other implementations are within the scope of the claims.

What is claimed is:

1. A sheet recognizing device which recognizes a sheet having a hue ink printed area in which a hue changes depending on a viewing angle, the sheet recognizing device comprising:

a first light source for switching and projecting light of a plurality of colors at a predetermined angle to a surface of the sheet;

a second light source for switching and projecting light of a plurality of colors from a vertical direction to the surface of the sheet;

a first light-receiving element for receiving a light from the first light source and reflected on the surface of the sheet at the angle at which the hue of the hue ink printed area changes;

a third light source for switching and projecting light of a plurality of colors at a predetermined angle to the back of the sheet;

a second light-receiving element for receiving a light from the third light source and reflected on the back of the sheet at the angle at which the hue of the hue ink printed area changes;

a third light-receiving element which is disposed on the back of the sheet so as to be opposite to the second light source;

first computing means for computing a first color tone depending on the hue ink printed area on the basis of each light-reception output that is output corresponding to a light-reception amount received by the first light-receiving element based on a color of light from the first light source, or on the basis of each light-reception output that is output corresponding to a light-reception amount received by the second light-receiving element based on a color of light from the third light source;

second computing means for computing a second color tone independent of the hue ink printed area on the basis of each light-reception output that is output corresponding to a light-reception amount received by the first light-receiving element based on a color of light from the second light source, or on the basis of each light-reception output that is output corresponding to a light-reception amount received by the third light-receiving element based on a color of light from the third light source; and sheet discriminating means for discriminating the sheet on the basis of results of the computation performed by the first computing means and the second computing means.

2. The sheet recognizing device according to claim 1, wherein the first light source, the second light source, and the third light source are each a two-color light-emitting source for switching and emitting red and green light beams, the first computing means computes a first ratio which is a ratio between the light-reception output from the first light-receiving element when the first light source emits the red light beam and the light-reception output from the first light-receiving element when the first light source emits the green light beam, or a ratio between the light-reception output from the second light-receiving element when the third light source emits the red light beam and the light-reception output from the second light-receiving element when the third light source emits the green light beam, the second computing means computes a second ratio which is a ratio between the light-reception output from the first light-receiving element when the second light source emits the red light beam and the light-reception output from the first light-receiving element when the second light source emits the green light beam, or a ratio between the light-reception output from the third light-receiving element when the third light source emits the red light beam and the light-reception output from the third light-receiving element when the third light source emits the green light beam, and the sheet discriminating means computes a ratio between the first ratio and the second ratio to discriminate the sheet on the basis of the value of the ratio between the first ratio and the second ratio.

3. The sheet recognizing device according to claim 2, further comprising:

bill type and insertion direction discriminating means for discriminating front and back sides, forward and reverse insertion directions, and a bill type of the sheet;

watermark area specifying means for specifying a watermark area of the sheet on the basis of a discrimination output from the bill type and insertion direction discriminating means;

maximum light-reception output detecting means for detecting a maximum light-reception output in which the sum of the light-reception output from the first light-receiving element when the first light source emits the red light beam and the light-reception output from the first light-receiving element when the first light source emits the green light beam is the maximum, and a maximum light-reception output in which the sum of the light-reception output from the first light-receiving element when the second light source emits the red light beam and the light-reception output from the first light-receiving element when the second light source emits the green light beam is the maximum, or a maximum light-reception output in which the sum of the light-reception output from the second light-receiving element when the third light source emits the red light beam and the light-reception output from the second light-receiving element when the third light source emits the green light beam is the maximum, and a maximum light-reception output in which the sum of the light-reception output from the third light-receiving element when the third light source emits the red light beam and the light-reception output from the third light-receiving element when the third light source emits the green light beam is the maximum, each of the maximum light-reception outputs being in the watermark area specified by the watermark area specifying means; and correcting means for correcting the light-reception outputs of the first light-receiving element, the second light-receiving element, and the third light-receiving element on the basis of the maximum light-reception outputs detected by the maximum light-reception output detecting means.

4. The sheet recognizing device according to claim 3, wherein the correcting means corrects the red light-reception output of each of the light-receiving elements on the basis of a red light-reception output at a position in which the maximum light-reception output is detected by the maximum light-reception output detecting means, and corrects the green light-reception output detected in the light-receiving element on the basis of a green light-reception output at a position in which the maximum light-reception output is detected by the maximum light-reception output detecting means.

5. The sheet recognizing device according to claim 3 or 4, wherein the sheet discriminating means further comprises:

first discriminating means for discriminating the sheet on the basis of the value of the ratio between the first ratio computed by the first computing means and the second ratio computed by the second computing means;

second discriminating means for discriminating whether the bill type and insertion direction of the sheet are discriminated by the bill type and insertion direction discriminating means; and third discriminating means for discriminating the sheet through a watermark pattern of the sheet based on the light-reception output of the third light-receiving element when the second light source emits a red light beam and based on the light-reception output of the third light-receiving element when the second light source emits a green light beam, in the watermark area, and wherein the sheet is discriminated on the basis of results of the discrimination performed by the first discriminating means through the third discriminating means.

6. A sheet recognizing method of recognizing a sheet having a hue ink printed area in which hues change depending on a viewing angle, comprising:

disposing;

a first light source for switching and projecting light of a plurality of colors at a predetermined angle to a surface of the sheet, a second light source for switching and projecting light of a plurality of colors from a vertical direction to the surface of the sheet, a first light-receiving element for receiving a light from the first light source and reflected on the surface of the sheet at the angle at which the hue of the hue ink printed area changes, a third light source for switching and projecting light of a plurality of colors at a predetermined angle to the back of the sheet, a second light-receiving element for receiving a light from the third light source and reflected on the back of the sheet at the angle at which the hue of the hue ink printed area changes, and a third light-receiving element which is disposed on the back of the sheet so as to be opposite to the second light source, computing a first color tone depending on the hue ink printed area by first computing means on the basis of each light-reception output from the first light-receiving element or each light-reception output from the second light-receiving element, the first light-receiving element receiving each reflection light that is originated from the plural colors of light switched and projected by the first light source and is reflected on the surface of the sheet and outputting a received amount of each of the reflection light as the light-reception output, or the second light-receiving element receiving each reflection light that is originated from the plural colors of light switched and projected by the third light source and is reflected on the surface of the sheet and outputting a received amount of each of the reflection light as the light-reception output, computing a second color tone independent of the hue ink printed area by second computing means on the basis of each light-reception output from the first light-receiving element or each light-reception output from the third light-receiving element, the first light-receiving element receiving each reflection light that is originated from the plural colors of light switched and projected by the second light source and is reflected on the surface of the sheet and outputting a received amount of each of the reflection light as the light-reception output, or the third light-receiving element receiving each reflection light that is originated from the plural colors of light switched and projected by the third light source and is reflected on the surface of the sheet and outputting a received amount of each of the reflection light as the light-reception output, and discriminating the sheet by sheet discriminating means on the basis of results of the computation performed by the first computing means and the second computing means.

7. The sheet recognizing method according to claim 6, wherein the first light source, the second light source, and the third light source are each a two-color light-emitting source for switching and emitting red and green light beams, the first computing means computes a first ratio, which is a ratio between the light-reception output from the first light-receiving element when the first light source emits the red light beam and the light-reception output from the first light-receiving element when the first light source emits the green light beam, or a ratio between the light-reception output from the second light-receiving element when the third light source emits the red light beam and the light-reception output from the second light-receiving element when the third light source emits the green light beam, the second computing means computes a second ratio, which is a ratio between a light-reception output from the first light-receiving element when the second light source emits the red light beam and a light-reception output from the first light-receiving element when the second light source emits the green light beam, or a ratio between a light-reception output from the third light-receiving element when the third light source emits the red light beam and a light-reception output from the third light-receiving element when the third light source emits a green light beam, and the sheet discriminating means discriminates the sheet on the basis of a value of a ratio between the first ratio and the second ratio.

8. The sheet recognizing method according to claim 7, further comprising:

discriminating, by bill type and insertion direction discriminating means, front and back sides, forward and reverse insertion directions, and a bill type of the sheet;

specifying, by watermark area specifying means, a watermark area of the sheet, on the basis of a discrimination by the bill type and insertion direction discriminating means;

detecting, by maximum light-reception output detecting means, a maximum light-reception output in which the sum of the light-reception output from the first light-receiving element when the first light source emits the red light beam and the light-reception output from the first light-receiving element when the first light source emits the green light beam is the maximum, and a maximum light-reception output in which the sum of the light-reception output from the first light-receiving element when the second light source emits the red light beam and the light-reception output from the first light-receiving element when the second light source emits the green light beam is the maximum, or a maximum light-reception output in which the sum of the light-reception output from the second light-receiving element when the third light source emits the red light beam and the light-reception output from the second light-receiving element when the third light source emits the green light beam is the maximum, and a maximum light-reception output in which the sum of the light-reception output from the third light-receiving element when the third light source emits the red light beam and the light-reception output from the third light-receiving element when the third light source emits the green light beam is the maximum, each of the maximum light-reception outputs being in the watermark area specified by the watermark area specifying means; and correcting, by correcting means, the light-reception outputs of the first light-receiving element, the second light-receiving element, and the third light-receiving element on the basis of the maximum light-reception outputs detected by the maximum light-reception output detecting means.

9. The sheet recognizing method according to claim 8, wherein the correcting means corrects the red light-reception output of each of the light-receiving elements on the basis of a red light-reception output at a position in which the maximum light-reception output is detected by the maximum light-reception output detecting means, and corrects the green light-reception output detected in each of the light-receiving elements, on the basis of a green light-reception output at a position in which the maximum light-reception output is detected by the maximum light-reception output detecting means.

10. The sheet recognizing method according to claim 8 or 9, wherein the sheet discriminating means further comprises:

discriminating, by first discriminating means, the sheet on the basis of the value of the ratio between the first ratio computed by the first computing means and the second ratio computed by the second computing means;

discriminating, by second discriminating means, whether the bill type and insertion direction of the sheet are discriminated by the bill type and insertion direction discriminating means;

discriminating, by third discriminating means, the sheet through a watermark pattern of the sheet based on the light-reception output of the third light-receiving element when the second light source emits the red light beam and based on the light-reception output of the third light-receiving element when the second light source emits the green light beam, in the watermark area; and discriminating the sheet on the basis of results of the discrimination performed by the first discriminating means through the third discriminating means.

* * * * *